US012060574B2

(12) United States Patent
Mitrani

(10) Patent No.: US 12,060,574 B2
(45) Date of Patent: *Aug. 13, 2024

(54) METHODS OF GENERATING TISSUE USING DEVITALIZED, ACELLULAR SCAFFOLD MATRICES DERIVED FROM MICRO-ORGANS

(71) Applicant: YISSUM RESEARCH DEVELOPMENT COMPANY OF THE HEBREW UNIVERSITY OF JERUSALEM LTD., Jerusalem (IL)

(72) Inventor: Eduardo N. Mitrani, Jerusalem (IL)

(73) Assignee: YISSUM RESEARCH DEVELOPMENT COMPANY OF THE HEBREW UNIVERSITY OF JERUSALEM LTD., Jerusalem (IL)

( * ) Notice: Subject to any disclaimer, the term of this patent is extended or adjusted under 35 U.S.C. 154(b) by 1425 days.

This patent is subject to a terminal disclaimer.

(21) Appl. No.: 16/124,901

(22) Filed: Sep. 7, 2018

(65) Prior Publication Data

US 2018/0371407 A1 Dec. 27, 2018

Related U.S. Application Data

(63) Continuation of application No. 13/147,221, filed as application No. PCT/IL2010/000076 on Jan. 31, 2010, now Pat. No. 10,093,896.

(60) Provisional application No. 61/202,307, filed on Feb. 17, 2009.

(30) Foreign Application Priority Data

Feb. 1, 2009 (IL) .......................................... 196820

(51) Int. Cl.
| C12N 5/00 | (2006.01) |
| A61L 27/36 | (2006.01) |
| A61L 27/38 | (2006.01) |
| C12N 5/071 | (2010.01) |
| C12N 5/0735 | (2010.01) |
| A61K 35/12 | (2015.01) |

(52) U.S. Cl.
CPC ........ *C12N 5/0068* (2013.01); *A61L 27/3604* (2013.01); *A61L 27/3804* (2013.01); *C12N 5/0606* (2013.01); *C12N 5/067* (2013.01); *C12N 5/0676* (2013.01); *C12N 5/0677* (2013.01); *C12N 5/0689* (2013.01); *A61K 35/12* (2013.01); *C12N 2506/02* (2013.01); *C12N 2533/90* (2013.01)

(58) Field of Classification Search
CPC .. C12N 5/0068; C12N 5/0676; C12N 5/0677; C12N 5/0689; C12N 2533/90; A61L 27/3804; A61L 27/3604; A61K 35/12
See application file for complete search history.

(56) References Cited

U.S. PATENT DOCUMENTS

| 3,791,932 | A | 2/1974 | Schuurs |
| 3,839,153 | A | 10/1974 | Schuurs |
| 3,850,578 | A | 11/1974 | McConnell |
| 3,850,752 | A | 11/1974 | Schuurs |
| 3,853,987 | A | 12/1974 | Dreyer |
| 3,867,517 | A | 2/1975 | Ling |
| 3,879,262 | A | 4/1975 | Schuurs |
| 3,901,654 | A | 8/1975 | Gross |
| 3,935,074 | A | 1/1976 | Rubenstein |
| 3,984,533 | A | 10/1976 | Uzgiris |
| 3,996,345 | A | 12/1976 | Ullman |
| 4,034,074 | A | 7/1977 | Miles |
| 4,098,876 | A | 7/1978 | Piasio |
| 4,666,828 | A | 5/1987 | Gusella |
| 4,683,202 | A | 7/1987 | Mullis |
| 4,801,531 | A | 1/1989 | Frossard |
| 4,879,219 | A | 11/1989 | Wands |
| 5,011,771 | A | 4/1991 | Bellet |
| 5,192,659 | A | 3/1993 | Simons |
| 5,272,057 | A | 12/1993 | Smulson |
| 5,281,521 | A | 1/1994 | Trojanowski |
| 5,695,998 | A | 12/1997 | Badylak |
| 5,888,720 | A | 3/1999 | Mitrani |
| 6,472,200 | B1 | 10/2002 | Mitrani |
| 7,297,540 | B2 | 11/2007 | Mitrani |
| 7,427,415 | B2 | 9/2008 | Scharp |
| 2003/0113302 | A1 | 6/2003 | Revazova |
| 2004/0126405 | A1 | 7/2004 | Sahatjian |
| 2005/0048040 | A1 | 3/2005 | Powers |

(Continued)

FOREIGN PATENT DOCUMENTS

| WO | 99/49807 | 10/1999 |
| WO | 01/00859 | 1/2001 |

(Continued)

OTHER PUBLICATIONS

Scharfmann et al. Beta Cells within Single Human Islets Originate from Multiple Progenitors. PLoS One. 2008;3(10):e3559.*

(Continued)

*Primary Examiner* — Lynn Y Fan

(74) *Attorney, Agent, or Firm* — Wenderoth, Lind & Ponack, L.L.P.

(57) ABSTRACT

A composition of matter is provided comprising a devitalized, acellular tissue-derived scaffold seeded with differentiated cells, particularly pancreatic islet cells, wherein the cells can maintain cell-specific function or structure in culture on the scaffold. Methods of generating same and uses thereof are also provided.

12 Claims, 15 Drawing Sheets

Specification includes a Sequence Listing.

(56) References Cited

U.S. PATENT DOCUMENTS

| | | |
|---|---|---|
| 2006/0275900 A1 | 12/2006 | Presnell |
| 2008/0103606 A1 | 5/2008 | Berkland |
| 2009/0004238 A1 | 1/2009 | Scharp |
| 2009/0069903 A1 | 3/2009 | Shortkroff |
| 2009/0074732 A1 | 3/2009 | Badylak |
| 2009/0221068 A1 | 9/2009 | Kobayashi |

FOREIGN PATENT DOCUMENTS

| | | | |
|---|---|---|---|
| WO | 01/07098 | 2/2001 | |
| WO | WO 01/48153 | 7/2001 | |
| WO | 03/035851 | 5/2003 | |
| WO | WO 03/043674 | 5/2003 | |
| WO | 2003/060062 | 7/2003 | |
| WO | WO 03/060062 | 7/2003 | |
| WO | WO-2003060062 A2 * | 7/2003 | |
| WO | 2004/006831 | 1/2004 | |
| WO | 2004/078916 | 9/2004 | |
| WO | 2004/080175 | 9/2004 | |
| WO | 2004/080501 | 9/2004 | |
| WO | WO 2004/080175 | 9/2004 | |
| WO | WO 2004/080501 | 9/2004 | |
| WO | WO-2004080175 A2 * | 9/2004 | |
| WO | WO-2008008229 A2 * | 1/2008 | ............ A61K 35/12 |
| WO | WO 2010/086856 | 8/2010 | |

OTHER PUBLICATIONS

Guillam et al. Early diabetes and abnormal postnatal pancreatic islet development in mice lacking Glut-2. Nat Genet. 1997;17:327-330.*
Service et al., (2005) Hyperinsulinemic hypoglycemia with nesidioblastosis after gastric-bypass surgery. N Engl J Med 353(3): 249-54.
Shapiro et al., (2000) Islet transplantation in seven patients with type 1 diabetes mellitus using a glucocorticoid-free immunosuppressive regimen. N Engl J Med 343(4): 230-8.
Shinozuka et al., (2001) Altered expression of HES-1, BETA2/NeuroD, and PDX-1 is involved in impaired insulin synthesis induced by glucocorticoids in HIT-T15 cells. Biochem Biophys Res Commun 287(1): 229-35.
Sionov et al., (2015) Beta Cells Secrete Significant and Regulated Levels of Insulin for Long Periods when Seeded onto Acellular Micro-Scaffolds. Tissue Eng Part A 21(21-22): 2691-702.
Stefan et al., (1987) Stimulation of insulin secretion reveals heterogeneity of pancreatic B cells in vivo. J Clin Invest 80(1): 175-83.
Suarez-Pinzon (2005) Combination therapy with epidermal growth factor and gastrin induces neogenesis of human islet {beta}-cells from pancreatic duct cells and an increase in functional {beta}-cell mass. J Clin Endocrinol Metab 90(6): 3401-9.
Sun et al., (2007) Differentiation of bone marrow-derived mesenchymal stem cells from diabetic patients into insulin-producing cells in vitro. Chin Med J (Engl) 120(9): 771-6.
Takahashi and Yamanaka (2006) Induction of pluripotent stem cells from mouse embryonic and adult fibroblast cultures by defined factors. Cell 126(4): 663-76.
Tang et al., (2004) In vivo and in vitro characterization of insulin-producing cells obtained from murine bone marrow. Diabetes 53(7): 1721-32.
Tateishi et al., (2008) Generation of insulin-secreting islet-like clusters from human skin fibroblasts. J Biol Chem 283(46): 31601-7.
Uludag et al., (2000) Technology of mammalian cell encapsulation. Adv Drug Deliv Rev 42(1-2): 29-64.
Vogel (2008) Breakthrough of the year. Reprogramming Cells. Science 322(5909): 1766-7.
Yoshitomi and Zaret (2004) Endothelial cell interactions initiate dorsal pancreas development by selectively inducing the transcription factor Ptf1a. Development 131(4): 807-17.
Zhang et al., (2003) Adenovirus transduction induces expression of multiple chemokines and chemokine receptors in murine beta cells and pancreatic islets. Am J Transplant 3(10): 1230-41.
Zhang et al., (2009) Highly efficient differentiation of human ES cells and iPS cells into mature pancreatic insulin-producing cells. Cell Res 19(4): 429-38.
Zhou et al., (2008) In vivo reprogramming of adult pancreatic exocrine cells to beta-cells. Nature 455(7213): 627-32.
Office Action dated Feb. 8, 2005, issuing in U.S. Appl. No. 10/045,018.
Abraham et al., (2002) Insulinotropic hormone glucagon-like peptide-1 differentiation of human pancreatic islet-derived progenitor cells into insulin-producing cells. Endocrinology 143(8): 3152-61.
Badylak (2004) Xenogeneic extracellular matrix as a scaffold for tissue reconstruction. Transpl Immunol 12(3-4): 367-77.
Beattie et al., (2002) A novel approach to increase human islet cell mass while preserving beta-cell function. Diabetes 51(12): 3435-9.
Bissell and Radisky (2001) Putting tumours in context. Nat Rev Cancer 1(1): 46-54.
Boker et al., (2001) Human islet transplantation: update. World J Surg 25(4): 481-6.
Brennand and Melton (2009) Slow and steady is the key to beta-cell replication. J Cell Mol Med 13(3): 472-87.
Brubaker and Drucker (2004) Minireview: Glucagon-like peptides regulate cell proliferation and apoptosis in the pancreas, gut, and central nervous system. Endocrinology 145(6): 2653-9.
Caspi et al., (2007) Tissue engineering of vascularized cardiac muscle from human embryonic stem cells. Circ Res 100(2): 263-72.
Chick (1973) Beta cell replication in rat pancreatic monolayer cultures. Effects of glucose, tolbutamide, glucocorticoid, growth hormone and glucagon. Diabetes 22(9): 687-93.
De Carlo et al., (2010) Pancreatic acellular matrix supports islet survival and function in a synthetic tubular device: in vitro and in vivo studies. Int J Mol Med 25(2): 195-202.
De la Tour et al., (2001) Beta-cell differentiation from a human pancreatic cell line in vitro and in vivo. Mol Endocrinol 15(3): 476-83.
Dufour et al., (2005) Development of an ectopic site for islet transplantation, using biodegradable scaffolds. Tissue Eng 11(9-10): 1323-31.
Efrat (2008) Ex-vivo Expansion of Adult Human Pancreatic Beta-Cells. Rev Diabet Stud 5(2): 116-22.
Gao et al., (2003) Characterization of endocrine progenitor cells and critical factors for their differentiation in human adult pancreatic cell culture. Diabetes 52(8): 2007-15.
Gartner et al., (2006) Long-term in vitro growth of human insulin-secreting insulinoma cells. Neuroendocrinology 83(2): 123-30.
Grad-Itach et al., (2003) Liver micro-organs transcribe albumin and clotting factors and increase survival of 92% hepatectomized rats. J Hepatol 39(4): 552-8.
Hara et al., (2003) Transgenic mice with green fluorescent protein-labeled pancreatic beta-cells. Am J Physiol Endocrinol Metab 284(1): E177-83.
Hasson et al., (2005) A cell-based multifactorial approach to angiogenesis. J Vasc Res 42(1): 29-37.
Hasson et al., (2005) Solid tissues can be manipulated ex vivo and used as vehicles for gene therapy. J Gene Med 7(7): 926-35.
Hasson et al., (2006) Skin-derived micro-organs induce angiogenesis in rabbits. J Vasc Res 43(2): 139-48.
Hirshberg et al., (2003) Benefits and risks of solitary islet transplantation for type 1 diabetes using steroid-sparing immunosuppression: the National Institutes of Health experience. Diabetes Care 26(12): 3288-95.
Inoue et al., (2002) VEGF-A has a critical, nonredundant role in angiogenic switching and pancreatic beta cell carcinogenesis. Cancer Cell 1(2): 193-202.
Jansson and Carlsson (2002) Graft vascular function after transplantation of pancreatic islets. Diabetologia 45(6): 749-63.
Jensen et al., (2005) STAT5 activation by human GH protects insulin-producing cells against interleukin-1beta, interferon-gamma and tumour necrosis factor-alpha-induced apoptosis independent of nitric oxide production. J Endocrinol 187(1): 25-36.
Kaido et al., (2006) Impact of defined matrix interactions on insulin production by cultured human beta-cells: effect on insulin content, secretion, and gene transcription. Diabetes 55(10): 2723-9.

(56) References Cited

OTHER PUBLICATIONS

Kayali et al., (2007) Limited capacity of human adult islets expanded in vitro to redifferentiate into insulin-producing beta-cells. Diabetes 56(3): 703-8.
Kralj and Pavelic (2003) Medicine on a small scale. EMBO Rep 4(11): 1008-12.
Lammert et al., (2001) Induction of pancreatic differentiation by signals from blood vessels. Science 294(5542): 564-7.
Lammert et al., (2003) Role of VEGF-A in vascularization of pancreatic islets. Curr Biol 13(12): 1070-4.
Latour et al., (2007) GPR40 is necessary but not sufficient for fatty acid stimulation of insulin secretion in vivo. Diabetes 56(4): 1087-94.
LeCouter and Ferrara (2003) EG-VEGF and Bv8. a novel family of tissue-selective mediators of angiogenesis, endothelial phenotype, and function. Trends Cardiovasc Med 13(7): 276-82.
Leite et al., (2007) Fibronectin and laminin induce expression of islet cell markers in hepatic oval cells in culture. Cell Tissue Res 327(3): 529-37.
Levenberg et al., (2005) Engineering vascularized skeletal muscle tissue. Nat Biotechnol 23(7): 879-84.
Logsdon et al., (1985) Glucocorticoids increase amylase mRNA levels, secretory organelles, and secretion in pancreatic acinar AR42J cells. J Cell Biol 100(4): 1200-8.
Lowe (2003) "The matrix unloaded": implications for cytokine signaling in islets? Endocrinology 144(10): 4262-3.
Marchetti et al., (1994) Pulsatile insulin secretion from isolated human pancreatic islets. Diabetes 43(6): 827-30.
Matsumoto et al., (2001) Liver organogenesis promoted by endothelial cells prior to vascular function. Science 294(5542): 559-63.
Menger et al., (2001) Revascularization and Microcirculation of Freely Grafted Islets of Langerhans. Worl J Surg 25(4): 509-515.
Mirmalek-Sani et al., (2013) Porcine pancreas extracellular matrix as a platform for endocrine pancreas bioengineering. Biomaterials 34(22): 5488-95.
Mitrani et al., (2005) Epithelial-mesenchymal interactions allow for epidermal cells to display an in vivo-like phenotype in vitro. Differentiation 73(2-3): 79-87.
Murray et al., (2005) Preservation of glucose responsiveness in human islets maintained in a rotational cell culture system. Mol Cell Endocrinol 238(1-2): 39-49.
Negi et al., (2012) Analysis of beta-cell gene expression reveals inflammatory signaling and evidence of dedifferentiation following human islet isolation and culture. PLoS One 7(1): e30415; 11 pages.
Nielsen et al., (2001) Regulation of beta-cell mass by hormones and growth factors. Diabetes 50 Suppl 1: S25-9.
Nikolova et al., (2006) The vascular basement membrane: a niche for insulin gene expression and Beta cell proliferation. Dev Cell 10(3): 397-405.
Ogata et al., (2005) Betacellulin-delta4, a novel differentiation factor for pancreatic beta-cells, ameliorates glucose intolerance in streptozotocin-treated rats. Endocrinology 146(11): 4673-81.
Ott et al., (2008) Perfusion-decellularized matrix: using nature's platform to engineer a bioartificial heart. Nat Med 14(2): 213-21.
Pralong et al., (1990) Single islet beta-cell stimulation by nutrients: relationship between pyridine nucleotides, cytosolic Ca2+ and secretion. EMBO J 9(1): 53-60.
Rall et al., (1977) Glucocorticoids modulate the in vitro development of the embryonic rat pancreas. J Cell Biol 75(2 Pt 1): 398-409.
Scharp et al., (1973) The use of ficoll in the preparation of viable islets of langerhans from the rat pancreas. Transplantation 16(6): 686-9.
Schroeder et al., (2006) Differentiation of mouse embryonic stem cells to insulin-producing cells. Nat Protoc 1(2): 495-507.
International Search Report and the Written Opinion Dated Aug. 4, 2010 From the International Searching Authority Re. Application No. PCT/IL2010/000076.
Gershonowitz et al. "Development of A Scaled Up Liver Device Incorporating Cryo-Preserved Pig Liver Micro-Organs", Journal of Hepatology, XP004776473, 41(6): 950-956, Dec. 1, 2004.
Islets, SIUC, Pancreatic islets, 2002; 1.
Andersson A. Isolated mouse pancreatic islets in culture: effects of serum and different culture media on the insulin production of the islets, Diabetologia. 1978; 14:397-404.
Xiaohui et al. Small intestinal submucosa improves islet survival and function in vitro culture. Transplantation Proceedings. 2006; 38:1552-1558.
Bowen R. Functional anatomy of the endocrine pancreas. The Endocrine Pancreas. 2002.
The Free Dictionary. Beta cell. 2012.
Medical Dictionary. GLUT2 protein. 2012.
Oxford Dictionary of Biochemistry. Pdx1. 2012.
Gaballa et al. Grafting an acellular 3-dimensional collagen scaffold onto a non-transmural infarcted myocardium induces neo-angiogenesis and reduces cardiac remodeling. The Journal of Heart and Lung Transplantation. 2006; 25(8) : 946-954.
Office Action dated Mar. 13, 2017 from the Israel Patent Office Re. Application No. 214376 and a translation into English (6 pages).
Office Action dated Feb. 9, 2016 from the Israel Patent Office Re. Application No. 214376 and a translation into English.
Communication Pursuant to Article 94(3) EPC dated Dec. 1, 2015 from the European Patent Office re: Application No. 10708818.9.
Nielsen et a. Preservation of Beta Cell Function in Adult Human Pancreatic Islets for Several Months in vitro. Diabetologia 16(2):97-100 (1979).
Communication Pursuant to Article 94(3) EPC dated Dec. 23, 2014 from the European Patent Office re: Application No. 10708818.9.
Communication Pursuant to Article 94(3) EPC dated Jul. 31, 2012 from the European Patent Office re: Application No. 10708818.9.

* cited by examiner

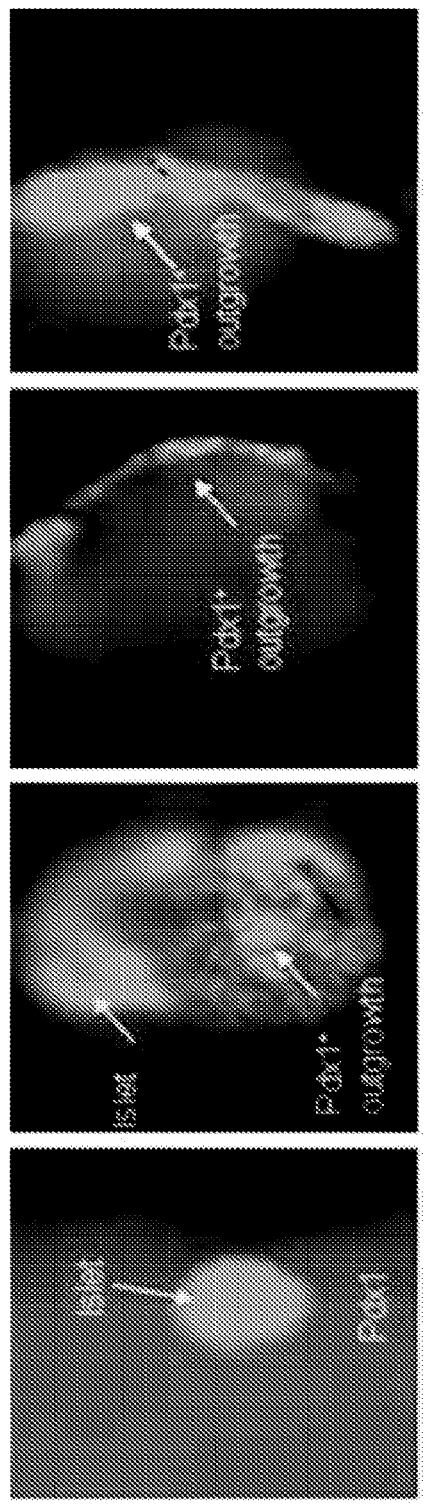
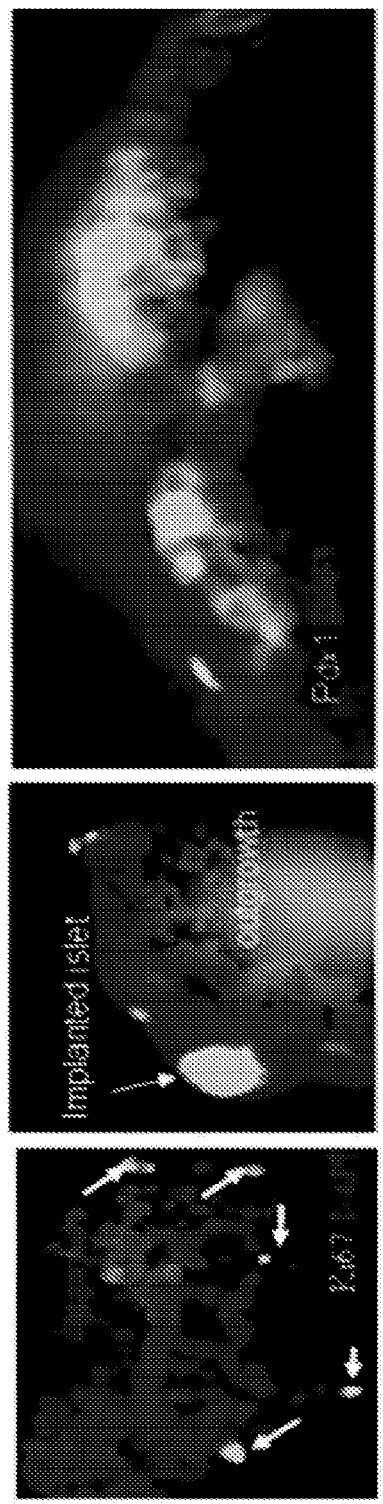

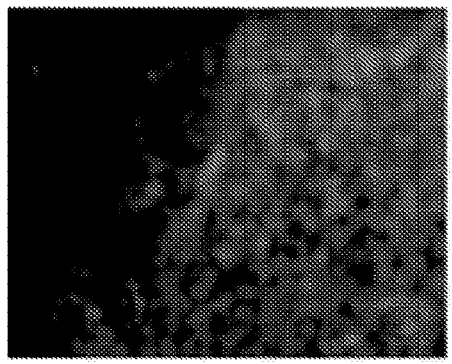
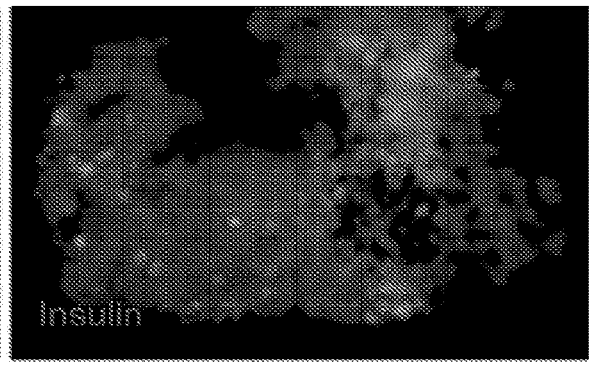
FIG. 6A      FIG. 6B
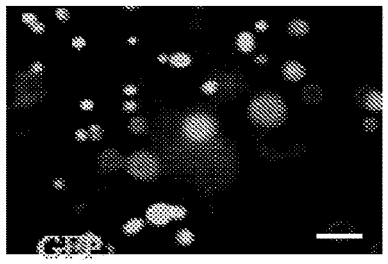
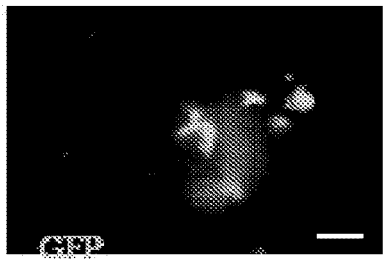
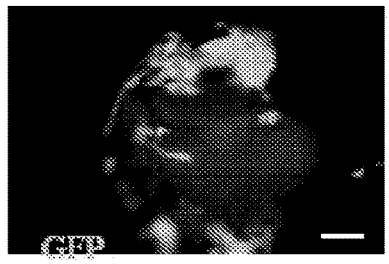
FIG. 7A      FIG. 7B      FIG. 7C
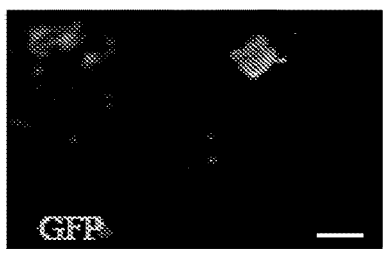
FIG. 7D      FIG. 7E      FIG. 7F
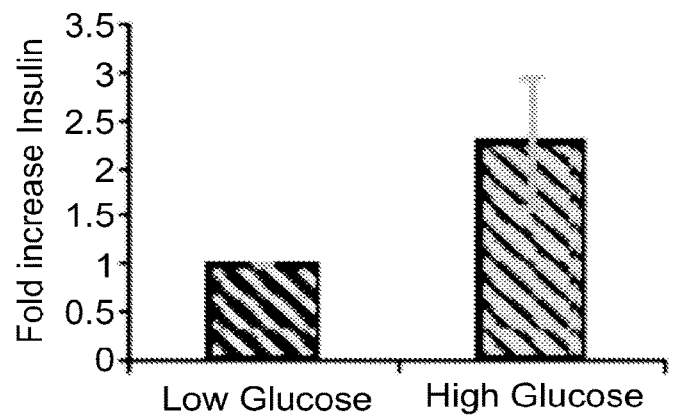
FIG. 8

14D
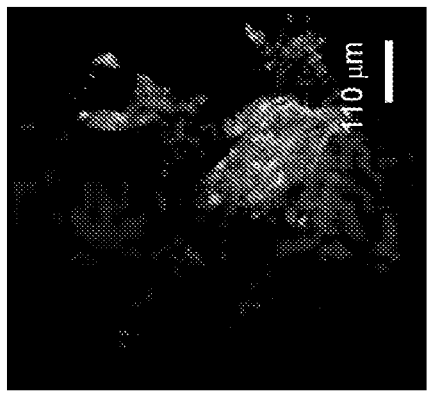
FIG. 10D
30D
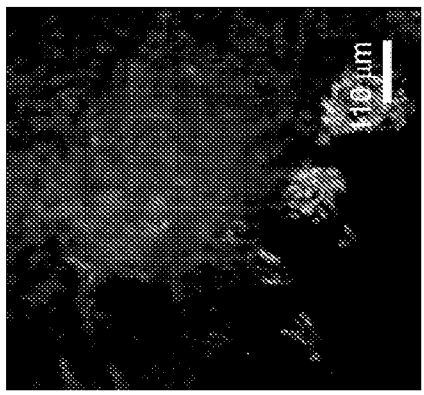
FIG. 10H
FIG. 10C
FIG. 10G
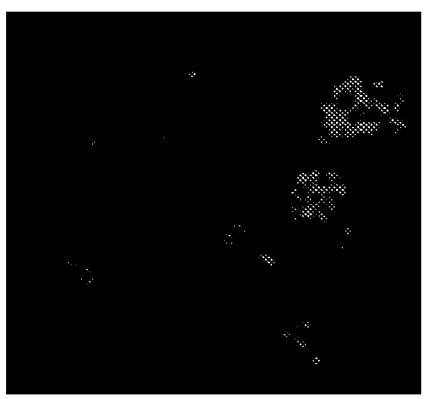
FIG. 10B
FIG. 10F
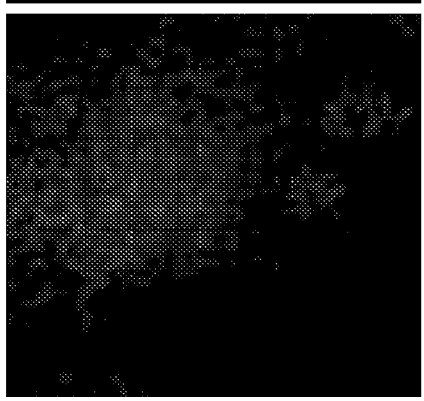
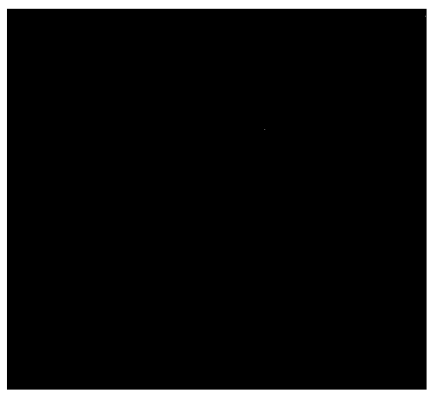
FIG. 10A
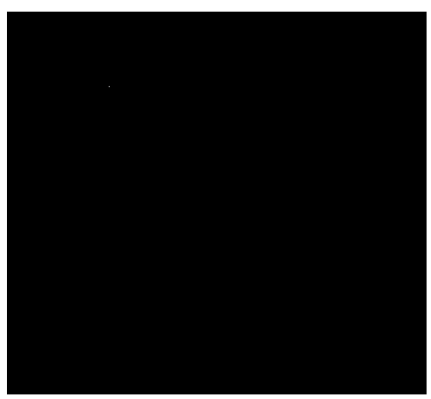
FIG. 10E
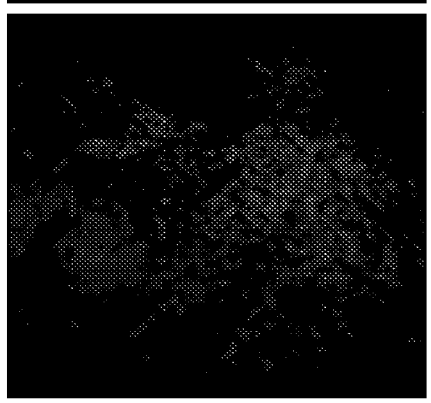

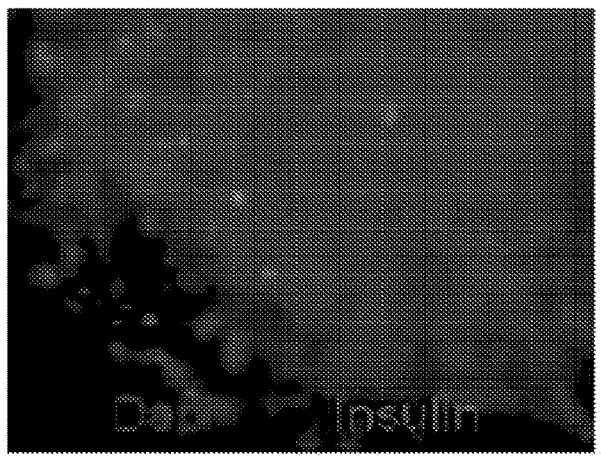 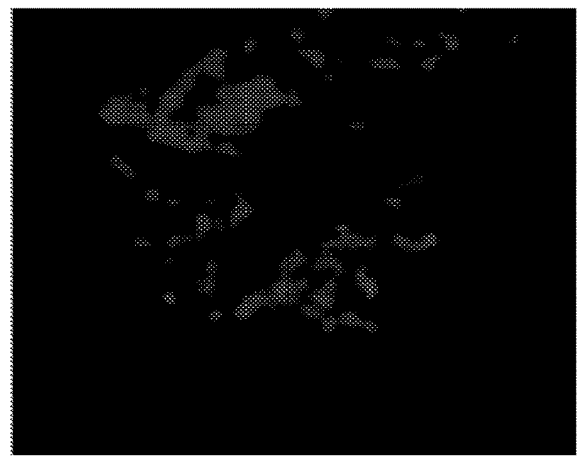
FIG. 12A  FIG. 12B
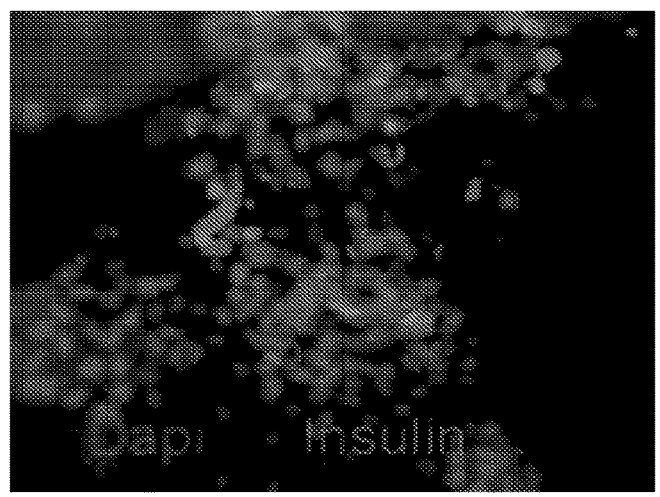
FIG. 13A
|  | Insulin | Albumin | Prosurfactant-B |
|---|---|---|---|
| Pancreas-MOM | + | - | - |
| Liver-MOM | + | + | n.d |
| Lung-MOM | - | - | n.d |
FIG. 13B

SEQUENCE LISTING

```
<160> NUMBER OF SEQ ID NOS: 22

<210> SEQ ID NO 1
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 1
taccacaggc attgtgatgg                                                   20

<210> SEQ ID NO 2
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 2
aatagtgatg acctggccgt                                                   20

<210> SEQ ID NO 3
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 3
acaccatcgc tacctttcc                                                    20

<210> SEQ ID NO 4
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 4
ctttccttta cagacttcca cc                                                22

<210> SEQ ID NO 5
<211> LENGTH: 20
<212> TYPE: DNA
<213> ORGANISM: Artificial sequence
<220> FEATURE:
<223> OTHER INFORMATION: Single strand DNA oligonucleotide
```

<400> SEQUENCE: 5
ttgccttctc ccactatcag       20

<210> SEQ ID NO 6
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 6
gccttatcat tccattgccc       20

<210> SEQ ID NO 7
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 7
tcatgctgtc catctgctgc       20

<210> SEQ ID NO 8
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 8
aaagaggaag gagggttcg       20

<210> SEQ ID NO 9
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 9
tgaagaagga ggtgtgttca g       21

<210> SEQ ID NO 10
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 10
tggtgttgtg ttgttgctg       19

<210> SEQ ID NO 11
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 11
tgaatctact ggcaaggcac       20

<210> SEQ ID NO 12
<211> LENGTH: 20

```
<212> TYPE: DNA
<213> ORGANISM: Artificial sequence
<220> FEATURE:
<223> OTHER INFORMATION: Single strand DNA oligonucleotide

<400> SEQUENCE: 12
acaggaagag gatggggaac                                                    20

<210> SEQ ID NO 13
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 13
aacacaaaga tgacaacccc                                                    20

<210> SEQ ID NO 14
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 14
ccaatgcttt ctccttcaca c                                                  21

<210> SEQ ID NO 15
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 15
gacaacccca gcatcaaac                                                     19

<210> SEQ ID NO 16
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 16
tagaagcagc cctatcagcc                                                    20

<210> SEQ ID NO 17
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 17
agctgaatgc acagtgatgg                                                    20

<210> SEQ ID NO 18
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 18
```

```
gaaaagccct gctcagtgtc                                                  20

<210> SEQ ID NO 19
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 19
ggcggatctg gagataatga                                                  20

<210> SEQ ID NO 20
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 20
catcaaaagg cttcctctgg                                                  20

<210> SEQ ID NO 21
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 21
tgtgtccatg cagaagaagc                                                  20

<210> SEQ ID NO 22
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 22
ggaaggtttc cccatcattt                                                  20
```

METHODS OF GENERATING TISSUE USING DEVITALIZED, ACELLULAR SCAFFOLD MATRICES DERIVED FROM MICRO-ORGANS

FIELD AND BACKGROUND OF THE INVENTION

The present invention, in some embodiments thereof, relates to methods for ex-vivo and in-vivo culture of cells, and, more particularly, but not exclusively, to the use of devitalized, acellular micro-organ matrices for culture of cells, tissue engineering and therapeutic uses thereof.

Micro-Organs (MOs)

Micro-organs provide an in vivo-like culture system based on the preparation of small organ fragments whose geometry allows preservation of the natural epithelial/mesenchymal interactions and ensures appropriate diffusion of nutrients and gases to all cells. These organ fragments have been termed micro-organs (MOs) since they preserve the basic organ architecture but are of microscopic thickness (300 µm). The thickness of MOs assures that no cell is more than about 150-250 µm away from a source of nutrients and gases. Since the micro-architecture is preserved, the natural cell-cell and cell-ECM interactions are maintained. MOs derived from several organs can be cultured for long periods in a minimal medium, and can thrive in the absence of serum or exogenous factors. During such periods, MOs remain viable, maintain the basic organ microstructure and express tissue specific genes. Preparation and use of MO is further described in detail in U.S. Pat. No. 5,888,720, and PCT Applications No. IL03/00578, IL00/00365, IL00/00424, IL 01/00976 and US98/00594, all of which are incorporated herein by reference.

U.S. Pat. No. 7,297,540, incorporated herein by reference, by the present inventors concerns methods of generating tissue using devitalized, acellular scaffold matrices derived from micro-organs, using stem cells/progenitor cells of adult or embryonic origin. Such cell free, three-dimensional scaffolds have been termed Micro-organ derived matrices (MOMs).

MO-derived matrices (MOMs) preserve both the 3-D architecture and the molecular composition of the stroma of the organ of origin. Due to their specific microscopic thickness, MOMs ensure that no seeded cell will be more than 100-250 microns from a source of gases and nutrients.

Diabetes

Diabetes mellitus is one of the most common chronic diseases in the world. In the United States, diabetes affects approximately 16 million people—more than 12% of the adult population over 45. The number of new cases is increasing by about 150,000 per year. In addition to those with clinical diabetes, there are approximately 20 million people showing symptoms of abnormal glucose tolerance. These people are borderline diabetics, midway between those who are normal and those who are clearly diabetic. Many of them will develop diabetes in time and some estimates of the potential number of diabetics are as high as 36 million or 25-30% of the adult population over 45 years.

Diabetes and its complications have a major socioeconomic impact on modem society. Of the approximately $700 billion dollars spent on healthcare in the US today, roughly $100 billion is spent to treat diabetes and its complications. Since the incidence of diabetes is rising, the costs of diabetes care will occupy an ever-increasing fraction of total healthcare expenditures unless steps are taken promptly to meet the challenge. The medical, emotional and financial toll of diabetes is enormous, and increase as the numbers of those suffering from diabetes grows.

Type 1 diabetes is characterized by loss and dysfunction of beta cells. Although the success rate of islet-cell transplantation has increased with experience, poor engraftment and the paucity of available islets remain a major limitation to widespread use of transplantation. In addition, longitudinal analyses of islet recipients make it clear that transplanted islets fail to maintain function (e.g. glucose responsive insulin secretion) over time. Therefore, promotion of beta cell formation, in-vitro and in-vivo, is a major goal of type 1 diabetes therapy.

Although beta cell culture has been demonstrated, production of significant numbers of viable and functional (glucose responsive) cultured beta cells for transplantation has not been achieved. In various animal models, the importance of the microenvironment for replication and differentiation of beta cells and beta cell precursors has been demonstrated. For example, repeated passage of nestin-positive islet progenitors in-vitro, without GLP-1, results in loss of insulin secretion capability. Further, even insulinoma cells required supporting fibroblast culture and pituitary adenoma cell conditioned medium to maintain insulin secretion in long-term culture. Similarly, pancreatic endocrine progenitor cells failed to differentiate in-vitro without a synthetic matrix overlay and, despite in-vitro proliferation of the differentiated, insulin-secreting cells, they failed to engraft and form functional islets when transplanted in-vivo.

In highly evolved organisms epithelial cells are always supported by a connective tissue stroma. Epithelial-stromal interactions play an important role in the maintenance of the structure and function of epithelial cells, both during normal development and also in the adult organism. It has recently been shown that this particularly dense vascular network is required for proper endocrine function and islet size. It has also been shown that in vivo, islets are surrounded by a continuous peri-insular basement membrane that contains collagen IV and laminin, which is lost during islet purification. Indeed, adding growth factors and extracellular-matrix factors, including laminin, nicotinamide and insulin, can lead to the formation of ES-derived progeny in culture resembling cells committed to the pancreatic lineage.

Alternatives to the inefficient and unsuccessful culture of beta cells in static, two dimensional conditions have been suggested.

One of the most likely reasons for the lack of success thus far in islet cell culture and transplantation is that islet cells require efficient perfusion, and, after transplantation, islet tissue grafts are dependent on extensive neo-vascularization for survival.

Native islets in the pancreas have a rich vascular structure thought to provide efficient delivery of oxygen and nutrients to islet cells and ensure rapid dispersal of pancreatic hormones to the circulation [Jansson, L. & Carlsson, P. O. Diabetologia 45, 749-763 (2002); Menger, M. D., Yamauchi, J. & Vollmar, B. World J Surg 25, 509-515 (2001)], which is not preserved in culture. Further, intra-islet endothelial cells are lost following 7 days of islet culture [Mendola, J. F. et al. Transplant Proc 26, 689-691 (1994); Parr, E. L., Bowen, K. M. & Lafferty, K. J. Transplantation 30, 135-141 (1980)], thus cultured islets are susceptible to ischemic injury (e.g., lack of oxygen or nutrients) upon transplantation. Therefore, rapid and adequate islet revascularization may be crucial for the survival and function of transplanted islets [Zhang N et al., Am J Transplant 3, 1230-1241 (2003)].

U.S. Patent Application No. 20050048040 teaches a method for enhancing vascularization of islets by increasing the quantity and/or quality of endothelial cells residing within. U.S. Patent Application No. 20030113302 also teaches a method for enhancing vascularization of islets by contact thereof with endothelial cells in the presence or absence of a scaffold.

U.S. Patent Application No. 20060275900 to Presnell et al. envisions transdifferentiation of non-beta acinar cells to an insulin producing phenotype by culturing with pancreatic specific differentiation factors. Rotary culture systems have provided slightly greater expansion but are impractical. U.S. Patent Application 20090069903, to Shortkroff et al. discloses a double structured tissue implant, comprising a primary porous collagen scaffold with a secondary soluble collagen hydrogel scaffold surrounding the seeded islets. U.S. Patent Application No. 20090221068 to Kobayashi et al also proposes a biodegradable peptide hydrogel scaffolding for culture of hepatic and pancreatic cells, and its use for transplantation. U.S. Patent Application 20040126405 to Sahatjian et al. discloses the use of non-woven, synthetic polymers for transplanatation and/or organ reconstruction, for example, of islet cells. U.S. Pat. No. 7,427,415 and Application 20090004238 to Scharp et al. propose transplantation of beta cells and islets encapsulated within synthetic polymers. U.S. Patent Application No. 20080103606 to Berkland et al. discloses the implantation of multilayered groups of pancreatic islets affixed to a synthetic planar support. U.S. Patent Application No. 20090074732 to Badylak discloses the use of acid-decellularized, heat treated parenchymous tissue as a scaffold for tissue implantation. Badylak provides no reduction to practice, and does not teach micro-organ scaffolds of defined dimensions, maintaining the original tissue architecture. However, none of the proposed solutions succeeded in providing conditions for successful culturing of functional (e.g. glucose responsive insulin secretion) islets and/or beta cells suitable for long-term survival and function in-vivo.

It is estimated that less than 30% of transplanted islet mass becomes stably engrafted, despite the administration of a large quantity of islets per diabetic recipient [Boker A. et al., World J Surg 25, 481-486 (2001)]. Given the limited supply of cadaveric donors and the prevalence of type 1 diabetes, there is a widely recognized need for, and it would be highly advantageous to have, methods for both efficient ex-vivo culture of pancreatic islets, and for providing viable cultured islets suitable for long-term survival and function following transplantation.

SUMMARY OF THE INVENTION

According to one aspect of the present invention there is provided a composition of matter comprising a devitalized, acellular, tissue-derived three dimensional scaffold, the acellular three dimensional scaffold being of dimensions selected such that the point deepest within the scaffold is at least about 100 micrometers and not more than about 225 micrometers away from the nearest surface of the scaffold and differentiated cells seeded on the acellular three dimensional scaffold, wherein the differentiated cells are selected from the group comprising pancreatic islet cells, lung cells and hepatocytes.

According to another aspect of the present invention there is provided an engineered micro-organ comprising a devitalized, acellular, tissue-derived three dimensional scaffold, the acellular three dimensional scaffold being of dimensions selected such that the point deepest within the scaffold is at least about 100 micrometers and not more than about 225 micrometers away from the nearest surface of the scaffold; and beta cells seeded on the acellular three dimensional scaffold, wherein the beta cells are characterized by glucose-responsive insulin secretion.

According to yet an additional aspect of the present invention there is provided an engineered micro-organ comprising a devitalized, acellular, tissue-derived three dimensional scaffold, the acellular three dimensional scaffold being of dimensions selected such that the point deepest within the scaffold is at least about 100 micrometers and not more than about 225 micrometers away from the nearest surface of the scaffold; and lung alveolar cells seeded on the acellular three dimensional scaffold, wherein the alveolar cells express at least one alveolar cell-specific protein when cultured.

According to one aspect of the present invention there is provided an engineered micro-organ comprising a devitalized, acellular, tissue-derived three dimensional scaffold, the acellular three dimensional scaffold being of dimensions selected such that the point deepest within the scaffold is at least about 100 micrometers and not more than about 225 micrometers away from the nearest surface of the scaffold; and hepatocytes seeded on the acellular three dimensional scaffold, wherein the hepatocytes express at least one liver specific protein selected from the group consisting of albumin, Factor V, α-GST, GS and MUP.

According to an additional aspect of the present invention there is provided a method of generating an engineered micro-organ, the method comprising seeding cells on a devitalized, acellular, tissue-derived three dimensional scaffold, the acellular three dimensional scaffold being of dimensions selected such that the point deepest within the scaffold is at least about 100 micrometers and not more than about 225 micrometers away from the nearest surface of the scaffold, wherein the cells are selected from the group consisting of pancreatic islet cells, hepatic cells and alveolar cells on the scaffold; and culturing the cells on the scaffold.

According to yet an additional aspect of the present invention there is provided a method of generating a composition of matter, the method comprising seeding cells on a devitalized, acellular, tissue-derived three dimensional scaffold, the acellular three dimensional scaffold being of dimensions selected such that the point deepest within the scaffold is at least about 100 micrometers and not more than about 225 micrometers away from the nearest surface of the scaffold, wherein the cells are selected from the group consisting of pancreatic islet cells, hepatic cells and alveolar cells.

According to still another aspect of the present invention there is provided a pharmaceutical composition comprising the composition of matter according to the invention and a pharmaceutically acceptable carrier.

According to yet an additional aspect of the present invention there is provided a pharmaceutical composition comprising the engineered micro-organ according to the invention and a pharmaceutically acceptable carrier.

According to one aspect of the present invention there is provided a method of treating diabetes in a subject, comprising transplanting a therapeutically effective amount of the engineered micro-organ of the invention into the subject, thereby treating diabetes.

According to another aspect of the present invention there is provided a method of treating diabetes in a subject, comprising transplanting a therapeutically effective amount of the engineered micro-organ of the invention into the subject, thereby treating diabetes.

According to an additional aspect of the present invention there is provided a method of treating an alveolar lung disease in a subject, comprising transplanting a therapeutically effective amount of the engineered micro-organ of any the invention into the subject, thereby treating the alveolar lung disease.

According to yet an additional aspect of the present invention there is provided a use of the engineered micro-organ of the invention for the manufacture of a medicament identified for the treatment of diabetes.

According to one aspect of the present invention there is provided a use of the engineered micro-organ of the invention for the manufacture of a medicament for treating an alveolar lung disease in a subject.

According to another aspect of the present invention there is provided a method of producing a pancreatic islet-cell specific protein comprising in-vitro culturing the engineered micro-organ of the invention under conditions which promote cell growth and proliferation, and isolating the islet cell-specific protein from the culture.

According to further features in preferred embodiments of the invention described below the protein is selected from the group consisting of insulin, Pdx1 and Glut2.

According to yet an additional aspect of the present invention there is provided a method of producing an alveolar-cell specific protein comprising in-vitro culturing the engineered micro-organ of the invention under conditions which promote cell growth and proliferation, and isolating the alveolar cell-specific protein from the culture.

According to yet further features in preferred embodiments of the invention described below the engineered micro-organ scaffold is generated from lung tissue and the protein is selected from the group consisting of surfactant-D, surfactant-C, prosurfactant-B, aquaporin 5 and T1-α.

According to still further features in preferred embodiments of the invention described below the pancreatic islet cells comprise beta cells.

According to further features in preferred embodiments of the invention described below the differentiated cells are of a different tissue than that from which the scaffold was derived.

According to yet further features in preferred embodiments of the invention described below the differentiated cells are prepared from live tissue.

According to still further features in preferred embodiments of the invention described below the differentiated cells are cultured cells.

According to further features in preferred embodiments of the invention described below the differentiated cells are pancreatic islet cells and the scaffold is derived from lung tissue.

According to yet further features in preferred embodiments of the invention described below differentiated cells are pancreatic islet cells, and the scaffold is derived from pancreatic tissue.

According to still further features in preferred embodiments of the invention described below the scaffold is produced by removing cells from a tissue section being of dimensions selected such that the point deepest within the scaffold is at least about 100 micrometers and not more than about 225 micrometers away from the nearest surface of the scaffold by treating the tissue by a method selected from the group consisting of alkaline treatment, detergent treatment and hyperosmotic conditions, so as to obtain a devitalized, acellular, tissue-derived three dimensional scaffold.

According to further features in preferred embodiments of the invention described below seeded cells express at least one cell-specific protein after at least 7 days in culture on the scaffolds.

According to yet further features in preferred embodiments of the invention described below the still beta cells are characterized by glucose-responsive insulin secretion after at least 7 days of culture on the micro-organ.

According to further features in preferred embodiments of the invention described below the beta cells are characterized by glucose-responsive insulin secretion after at least 14 days of culture on the micro-organ.

According to yet further features in preferred embodiments of the invention described below the beta cells are characterized by glucose-responsive insulin secretion after at least 28 days of culture on the micro-organ.

According to still further features in preferred embodiments of the invention described below the beta cells are characterized by glucose-responsive insulin secretion after at least 50 days of culture on the micro-organ.

According to further features in preferred embodiments of the invention described below the beta cells are characterized by glucose-responsive insulin secretion after at least 78 days of culture on the micro-organ.

According to yet further features in preferred embodiments of the invention described below the insulin secretion increases at least two fold when the micro-organ is first exposed to about 3 mM glucose and then exposed to about 16.7 mM glucose.

According to still further features in preferred embodiments of the invention described below the beta cells express Glut2 or Pdx1 following at least 7 days of culture on the micro-organ.

According to further features in preferred embodiments of the invention described below the beta cells express Glut2 or Pdx1 following at least 28 days of culture on the micro-organ.

According to yet further features in preferred embodiments of the invention described below the beta cells are prepared from live tissue.

According to still further features in preferred embodiments of the invention described below the beta cells are cultured beta cells.

According to still further features in preferred embodiments of the invention described below the beta cells are cultured and expanded beta cells.

According to further features in preferred embodiments of the invention described below the beta cells are comprised in islets.

According to yet further features in preferred embodiments of the invention described below the scaffold is a devitalized, acellular lung-derived scaffold.

According to still further features in preferred embodiments of the invention described below the scaffold is a devitalized, acellular pancreas-derived scaffold.

According to yet further features in preferred embodiments of the invention described below the alveolar cells are characterized by surfactant-C secretion after at least 8 days of culture on the micro-organ.

According to still further features in preferred embodiments of the invention described below the alveolar cells are characterized by surfactant-C secretion after at least 14 days of culture on the micro-organ.

According to further features in preferred embodiments of the invention described below the alveolar cells are characterized by surfactant-C secretion after at least 21 days of culture on the micro-organ.

According to yet further features in preferred embodiments of the invention described below the alveolar cells express an alveolar-specific protein selected from the group consisting of surfactant-D, prosurfactant-B, aquaporin 5 and T1-α after at least 8 days of culture on the micro-organ.

According to still further features in preferred embodiments of the invention described below the alveolar cells are prepared from live tissue.

According to further features in preferred embodiments of the invention described below the alveolar cells are cultured alveolar cells.

According to yet further features in preferred embodiments of the invention described below the scaffold is a devitalized, acellular lung-derived scaffold.

According to still further features in preferred embodiments of the invention described below the scaffold is a devitalized, acellular liver-derived scaffold and the alveolar cells express T1-α after at least 8 days of culture on the micro-organ.

According to further features in preferred embodiments of the invention described below the hepatocytes are characterized by secretion of at least one liver specific protein selected from the group consisting of albumin, Factor V, α-GST, GS and MUP after at least 8 days of culture on the micro-organ.

According to yet further features in preferred embodiments of the invention described below the hepatocytes are prepared from live tissue.

According to still further features in preferred embodiments of the invention described below the hepatocytes are cultured hepatocytes.

According to further features in preferred embodiments of the invention described below the scaffold is a devitalized, acellular liver-derived scaffold.

According to yet further features in preferred embodiments of the invention described below the scaffold is a devitalized, acellular lung-derived scaffold and the hepatocytes express FactorV after at least 8 days of culture on the micro-organ.

According to still further features in preferred embodiments of the invention described below when the cells are pancreatic islet cells, the acellular scaffold comprises devitalized lung tissue or devitalized pancreatic tissue.

According to yet further features in preferred embodiments of the invention described below when the cells are lung alveolar cells, the acellular scaffold comprises devitalized lung tissue or devitalized liver tissue.

According to further features in preferred embodiments of the invention described below the cells are hepatocytes, the acellular scaffold comprises devitalized liver tissue or lung tissue.

According to further features in preferred embodiments of the invention described below the acellular scaffold is prepared from cryopreserved tissue.

The present invention successfully addresses the shortcomings of the presently known configurations by providing cells cultured on devitalized, acellular micro-organ matrices for tissue engineering and therapeutic uses.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the patent specification, including definitions, will control. In addition, the materials, methods, and examples are illustrative only and not intended to be limiting.

BRIEF DESCRIPTION OF THE DRAWINGS

Some embodiments of the invention are herein described, by way of example only, with reference to the accompanying drawings and figures. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A and 1B are transmission electron microscope images of normal mouse lung tissue (1A) compared with lung MOMs (1B), showing retention of the alveolar spaces separated by septal walls (A1-A3). FIGS. 1C and 1D are cryostat, transverse sections of primary lung-derived mouse AII-P cells seeded into lung MOMs following 27 days culture. An epithelium has gradually formed (1C), lining the whole matrix including all alveolar cavities (bar=50 um). Nuclei are stained with DAPI (blue). Staining with fluorescent labeled anti-surfactant-B protein antibodies (1C, red), reveals alveolar cell function in about 30-50% of the cells lining each alveolus. Staining a prepared section of the micro-organ matrix with peroxidase-labeled surfactant B antibodies and hematoxylin and eosin counterstain (FIG. 1D, higher magnification) after 27 days culture reveals a remarkably natural alveolar structure, comprising both type 1 (squamous) alveolar cells and type 2 (greater), surfactant secreting alveolar cells (bar=30 um);

FIGS. 2A-2C demonstrate the gradual population of the lung-derived micro-organ matrix by AII-P lung progenitor cells (FIG. 2A=day 0; FIG. 2B=day 8 and FIG. 2C=day 21 of culture). Fluorescent staining for surfactant C protein (FIG. 2D) reveals localized expression of the lung-specific protein surfactant within the alveolar structure;

Figure 3A:
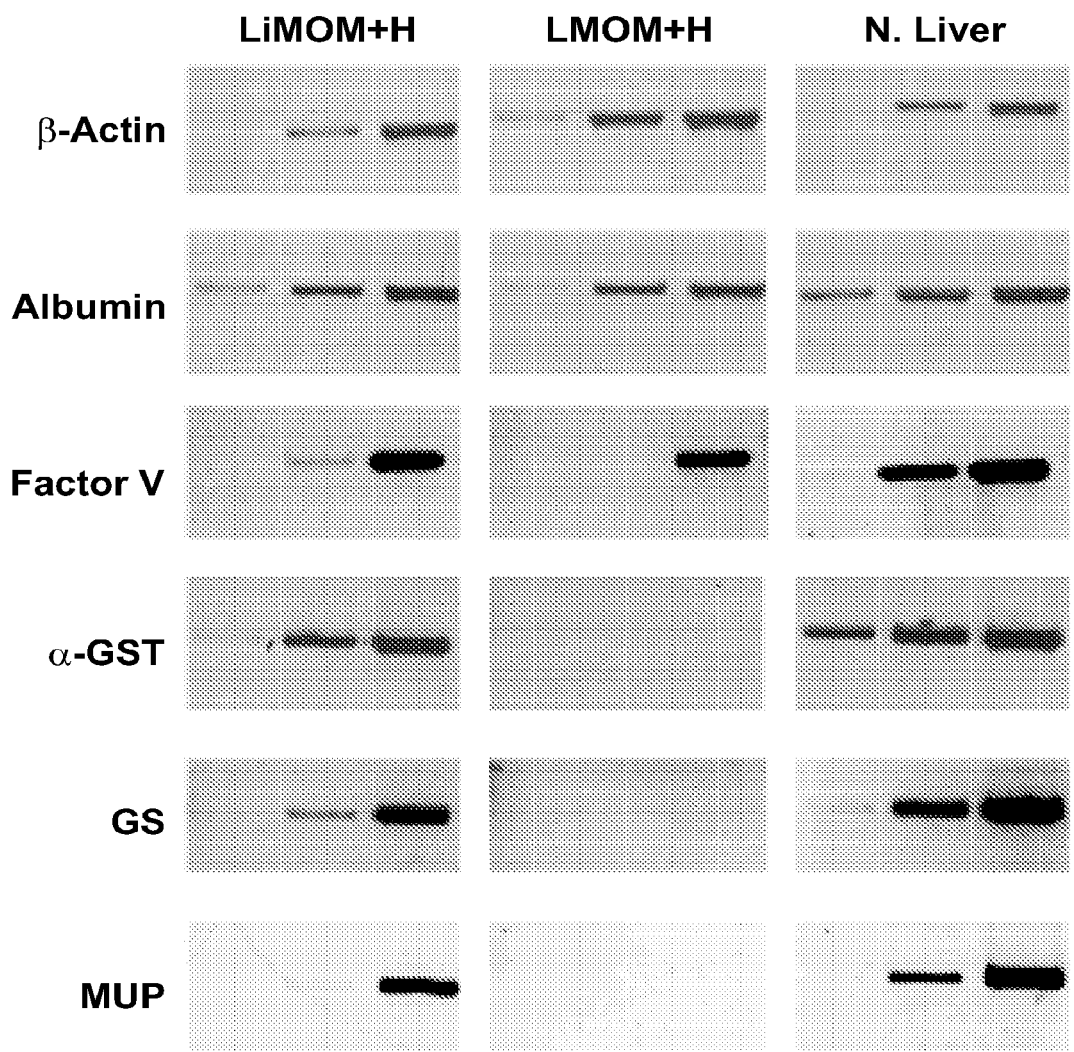
FIGS. 3A and 3B show a semi-quantitative RT-PCR analysis of gene expression from cultures comprising hepatocytes or AII-P alveolar progenitors seeded on liver or lung derived micro-organ matrices (MOMs). After culture for 21 days, expression of both housekeeping genes (β-actin) and liver specific genes (albumin, Factor V, α-GST, GS and MUP) was detected in primary hepatocytes (H) seeded on liver derived MOMs (LiMOM+H), while in primary hepatocytes (H) seeded on lung-derived MOMs (LMOM+H), no expression of the liver-specific genes α-GST (alpha glutathione-S-transferase), GS (glycogen synthase) and MUP (major urinary protein) could be detected (FIG. 3A). After seeding and incubation of cultured (3 passages prior to seeding on MOMs) lung AII-P alveolar progenitor cells for 21 days (FIG. 3B), expression of housekeeping genes (β-actin) and all of the lung specific genes (SP-C-surfactant C, SP-D-surfactant D, AQP-5-aquaporin-5 and T1-α-alveolar epithelial specific protein) was detected only in AII-P alveolar progenitors (AP) seeded on lung derived MOMs (LMOM+AP), while in AII-P alveolar progenitors (AP)
Figure 3B:
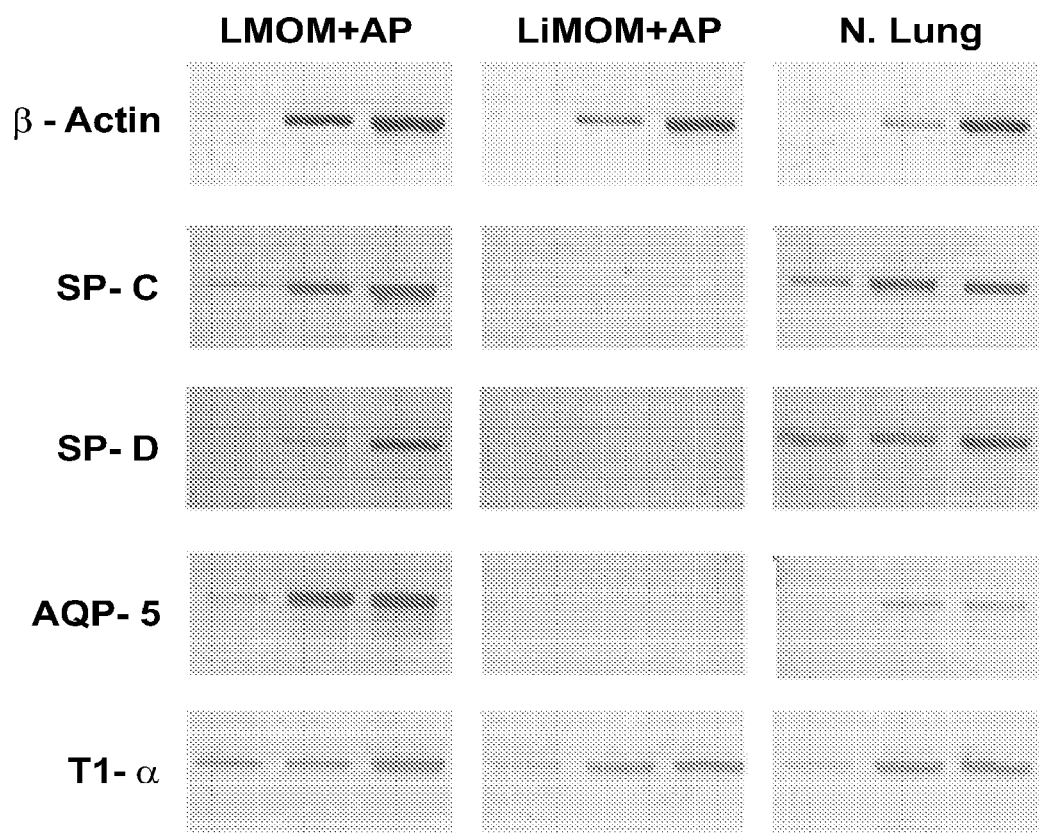
Figures 4A, 4B, 4C:
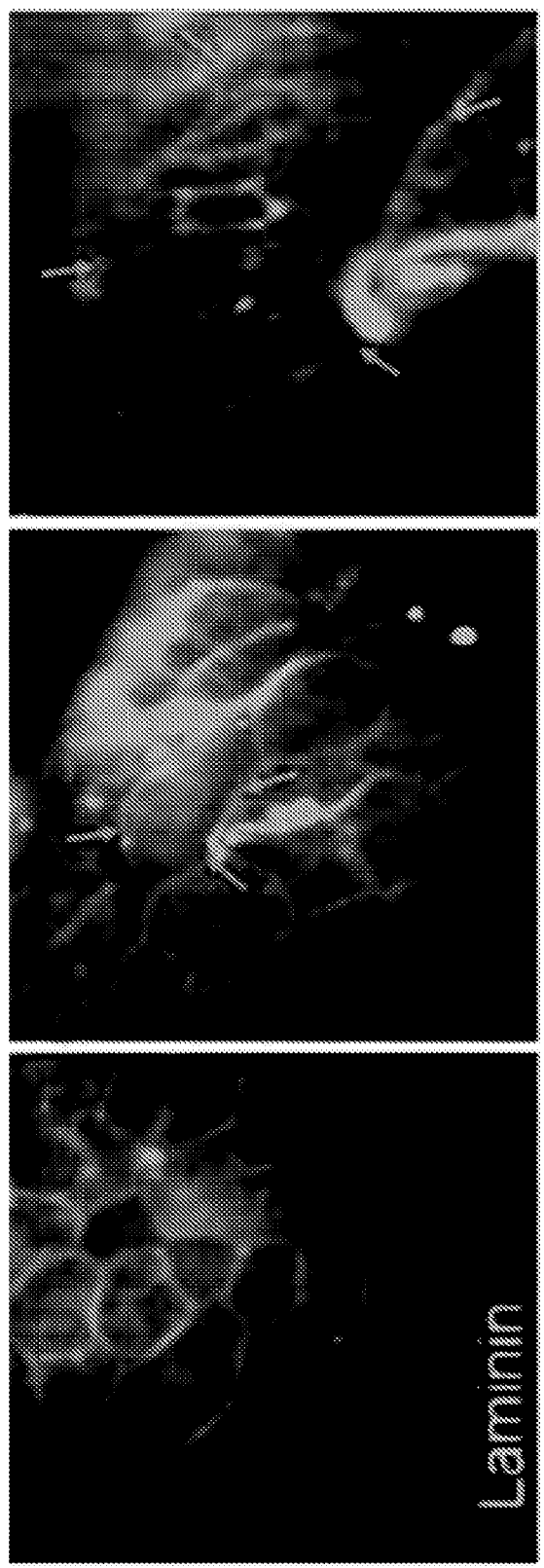
Figure 9A:
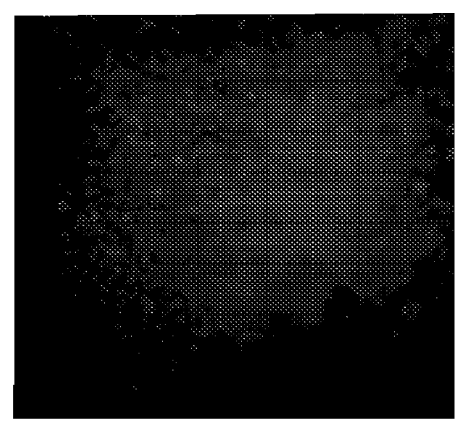
Figure 9B:
Figure 9C:
Figure 9D:
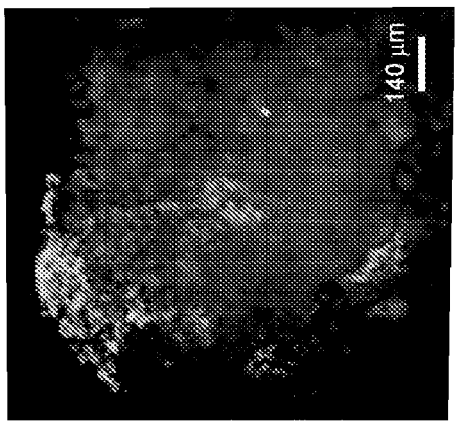
Figure 9E:
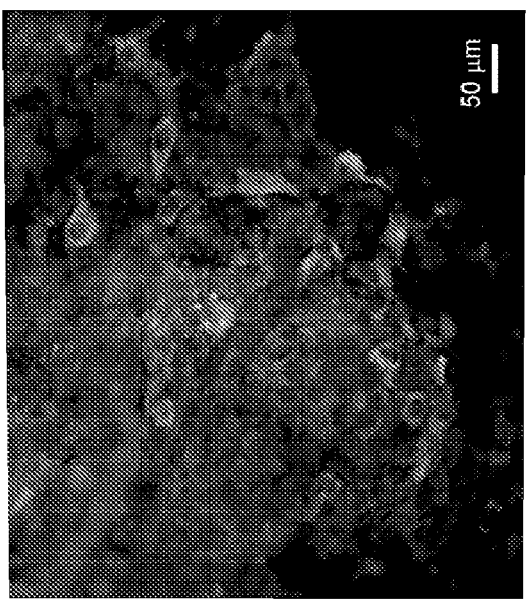
Figure 11:
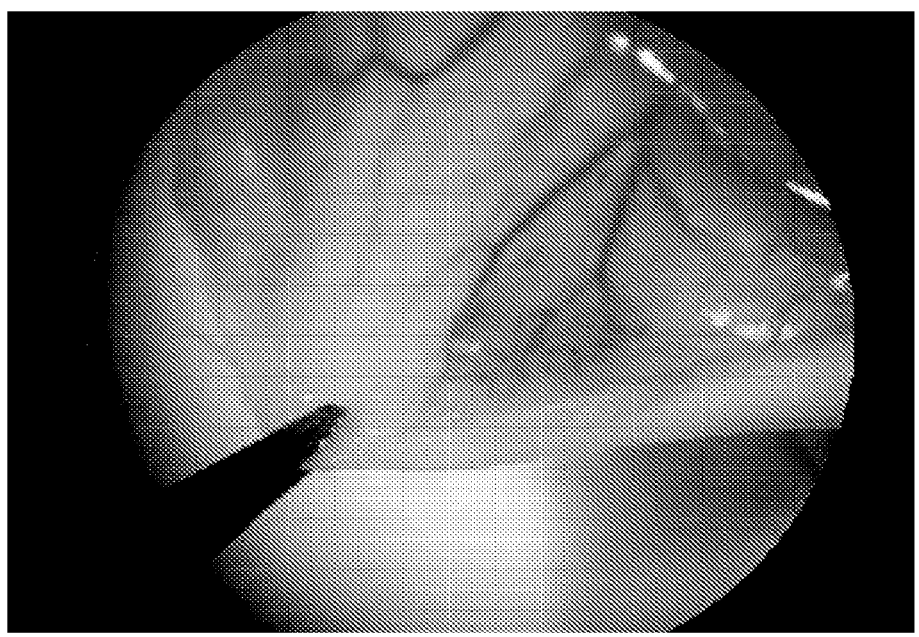
Figure 14A:
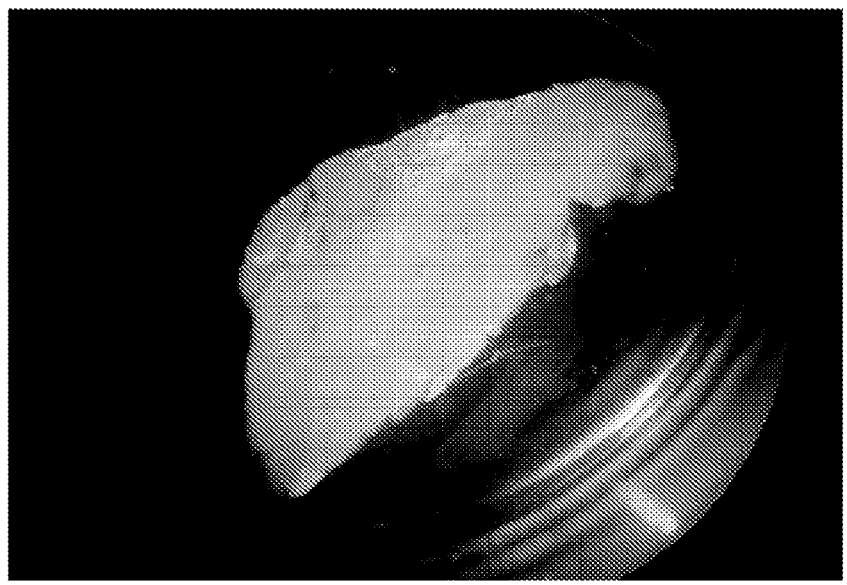
Figure 14B:
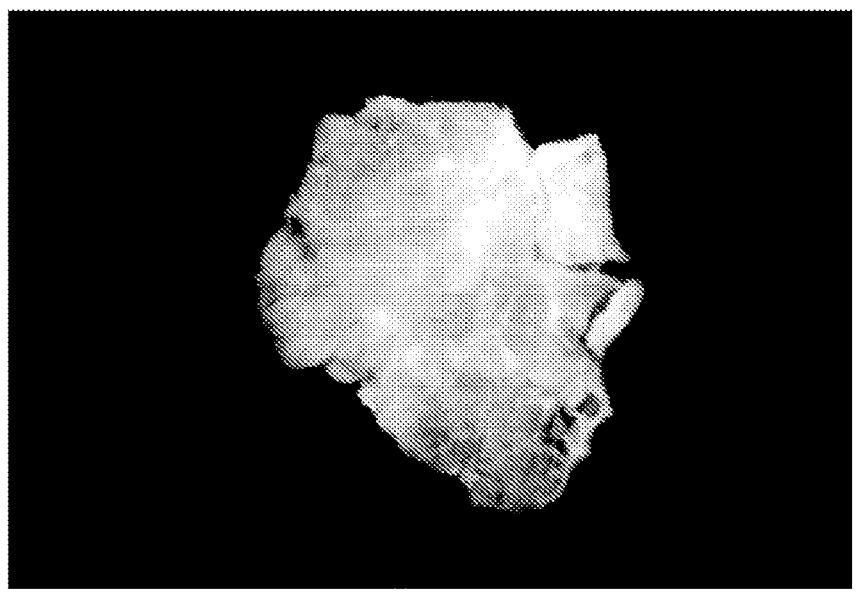

seeded on liver-derived MOMs (LiMOM+H) no expression of the lung-specific genes SP-C, SP-D and Aq-5 could be detected (FIG. 3B). N. lung and N. liver indicate expression results for normal lung and normal liver, respectively;

FIGS. 4A-4C are microscope images showing normal basement membrane pattern in pancreas-derived, cell-free micro-organ matrices (p-MOM). Acellular micro-organ matrices prepared from pancreata of adult C57/b1 mice demonstrate characteristic acinar organization. Staining of whole mounts of acellular p-MOMs for laminin shows typical acinar basement membrane (green) pattern (FIGS. 4A and 4B). Arrows (FIG. 4B) indicate the basement membrane surrounding an acinus and an islet. Higher magnification (FIG. 4C) reveals a characteristic acellular blood vessel pattern within the island;

FIGS. 5A-5G are a series of microscopic images showing the proliferation and gradual population by pancreatic islets after seeding on pancreas derived MOMs, and their retention of function in culture. When whole mouse-derived islets were seeded onto mouse p-MOMs, 1-2 islets were found to attach to each mouse p-MOM. Following 10 days in culture, the islet-MOM cultures were fixed and stained with DAPI for nuclei (dark blue) and the cell cycle marker Ki-67 (light blue) (FIG. 5E) to detect the proportion of cells cycling (arrows), and with the pancreatic cell marker Pdx1 (FIGS. 5A-5D, 5G, green) to detect beta cell development. Note the outgrowths of cells (FIGS. 5B, 5C, 5D and 5F) expressing Pdx-1 in the islet-MOM cultures;

FIGS. 6A-6B are microscope images showing formation of pancreas-like engineered organs from islet cells seeded on p-MOMs. FIG. 6A shows a transverse section through the cultured pMOM, 10 days after seeding with islets, indicating islet cells (DAPI, dark blue) in the depths of the MOM. FIG. 6B shows a lower magnification of the cultured islet-MOM after 78 days in culture, showing the entire MOM covered with cells. Note the diffuse insulin-secreting cells (red) at 10 days (FIG. 6A), compared with the dense cluster of insulin secreting cells (red) detected at 78 days (FIG. 6B);

FIGS. 7A-7F is a series of microscopic images showing the proliferation of dissociated islet cells on p-MOMs. Pancreatic islets from transgenic mice expressing GFP under transcriptional control of the islet-specific Pdx1 promoter were dissociated into suspension with trypsin and seeded onto pMOMs (30,000 cells/ml/well containing 4-6 p-MOMs). Diffuse GFP expression (green) is evident in live whole mount images of islet-pMOM after 1 day in culture (FIG. 7A), and progresses towards organization in clusters by day 13 (FIG. 7B), and more so at day 17 (FIG. 7C). For quantitation of GFP expression, islet-p-MOMs were fixed and stained with DAPI (dark blue) and anti-GFP(green) antibodies. After 11 days in culture, the proportion of GFP-expressing cells in the islet-pMOMs varied (see FIGS. 7D and 7E, showing about 20% and 50% GFP expressing cells, respectively). FIG. 7F shows a small cluster of GFP-producing cells in an 11 day islet-pMOM culture, at higher magnification;

FIG. 8 is a histogram showing glucose-responsive insulin secretion by islet-pMOMs. Islets seeded onto pMOMs as described for FIG. 5, and cultured 50 days, were transferred to serum free medium, rinsed and exposed to low (3 mM) glucose, rinsed and then exposed to high (16.7 mM) glucose medium. ELISA analysis of insulin in the medium revealed significant higher insulin secretion with increased glucose, indicating normal, glucose responsive beta cell function of the islets cultured on p-MOM scaffolds;

FIGS. 9A-9E is a series of microscopic images illustrating beta cell-specific function of islet cells in long-term lung-MOM culture. Isolated islet cells seeded on lung MOMs and cultured for 60 days were reacted with DAN (blue, specific for DNA FIG. 9A), and fluorescent antibodies against beta cell specific proteins insulin (red, FIG. 9B) and glucose transporter 2 (green, Glut2, FIG. 9C). Expression of insulin and Glut2 is concentrated in clusters of cells, and the patterns overlap nearly completely for the two proteins (FIG. 9D, and FIG. 9E, higher magnification);

FIGS. 10A-10H is a series of microscopic images showing proliferation and beta cell-specific function of islets in long term lung MOM culture. Islets seeded on lung MOMs and cultured for 14 (FIGS. 10A-10D) or 30 (FIGS. 10E-10H) days were stained with DAPI (blue, specific for DNA FIG. 9A), and fluorescent antibodies against the beta cell specific proteins insulin (red, FIGS. 10B and 10F) and glucose transporter 2 (green, Glut2, FIGS. 10C and 10G). Expression of insulin and Glut2 is concentrated in clusters of cells, and the patterns overlap nearly completely for the two proteins (FIG. 10D, and FIG. 10H);

FIG. 11 is a microscopic image showing vascularization of an islet—pMOM following implantation. Islet cell-pMOMs were cultured for 20 days ex-vivo, and implanted subcutaneously into a syngeneic mouse host. Observation of the islet-pMOM 15 days post-implantation revealed extensive vascularization of the implanted micro-organ matrix;

FIGS. 12A-12B are microscopic images showing cell outgrowth and pancreas-specific gene expression in hES cells grown on pancreas-derived MOMs. Human embryonic stem cells (hES) seeded on pancreatic-derived MOMs and cultured for 17 (FIG. 12A) or 20 (FIG. 12B) days were reacted with fluorescent antibodies specific for DNA (DAPI, blue) and insulin (red). FIG. 12A shows the expression of insulin in a live, whole mount hES-pMOM culture at 17 days. FIG. 12B is a 7 μm section of a hES-pMOM culture at 20 days. Note the concentration of insulin expressing cells in clusters;

FIGS. 13A-13B show the expression of tissue specific genes in hES cells grown on micro-organ matrices of diverse tissue origin. FIG. 13A shows the expression of insulin in a live, whole mount hES-pMOM culture at 17 days, reacted with (DAPI, blue, specific for DNA FIG. 9A), and fluorescent antibodies against insulin (red). FIG. 13B is a table showing partial selective differentiation of the hES cells by micro-organ matrix origin. Note that only liver, and not pancreas or lung MOMs induced albumin expression, and that only liver and pancreas, but not lung MOMs induced insulin expression;

FIGS. 14A and 14B are whole mounts of pig pancreas micro-organs, prepared from freshly frozen pancreata. FIG. 14A shows the 300 μm-thick micro-organ prepared from cryopreserved (−80° C.) pancreas tissue before decellularization. FIG. 14B shows the same micro-organ following decellularization.

Figure 15A:
Figure 15B:
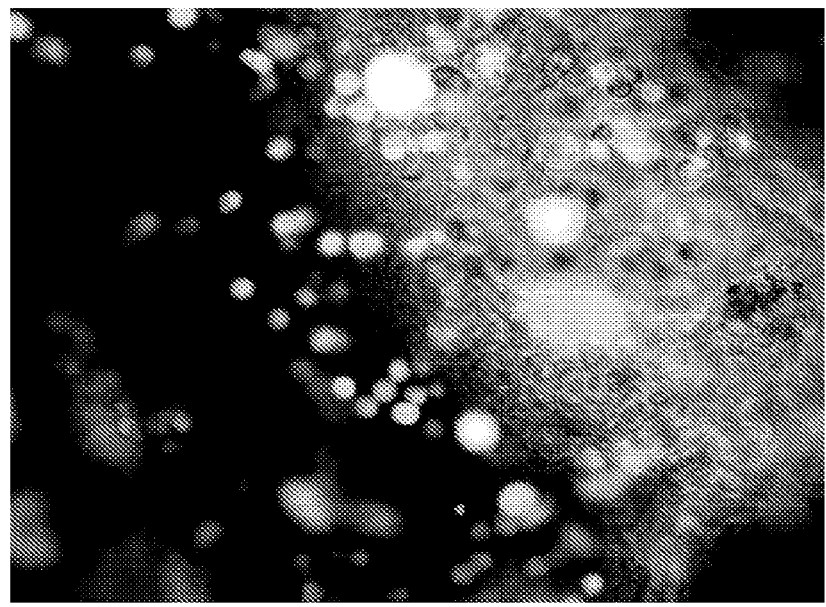
Figure 15C:
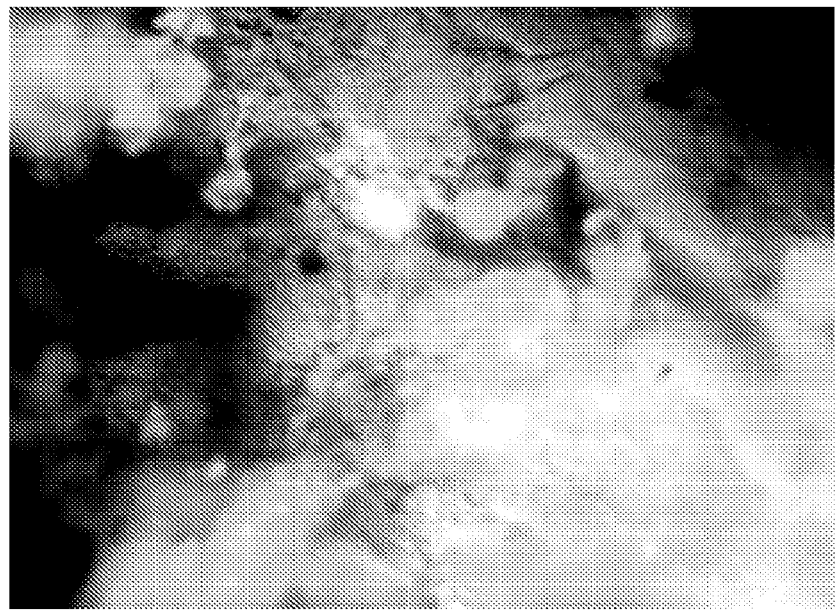
Figure 15D:
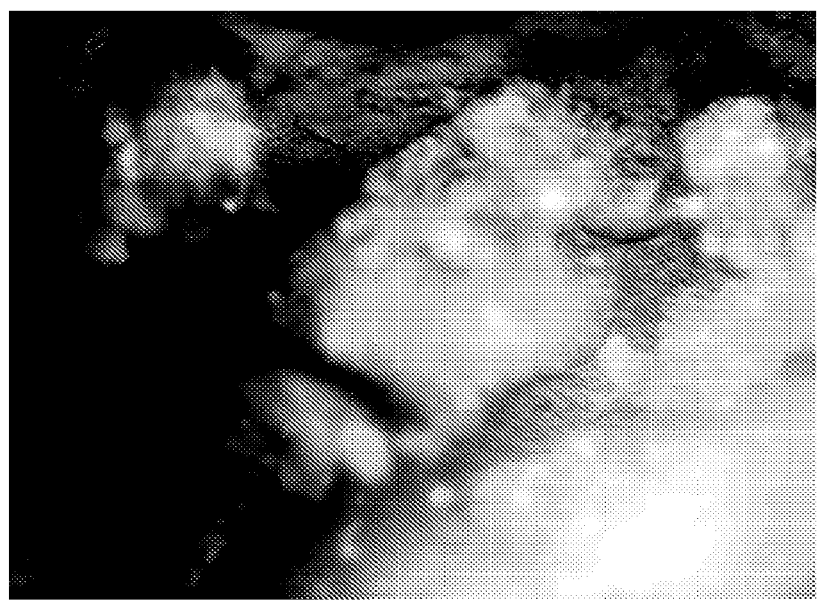
Figure 15E:
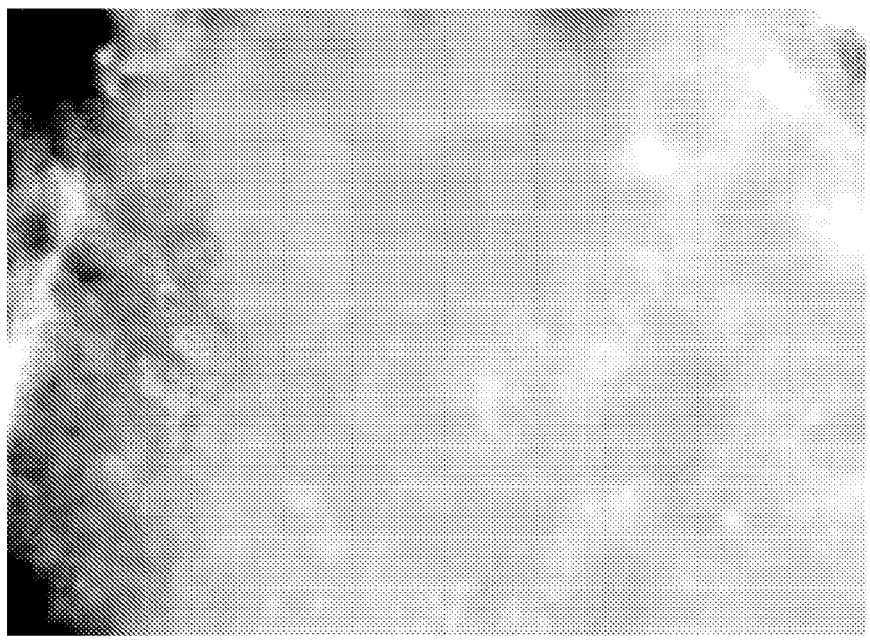
Figure 15F:
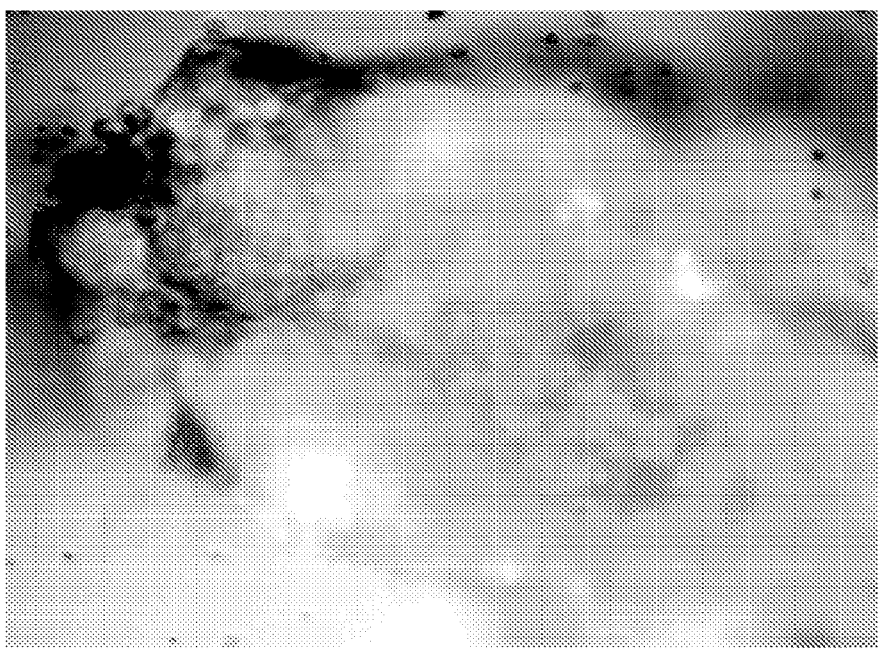

FIGS. 15A-15F are a series of micrographs showing the long term growth of human breast carcinoma-GFP cells on large scale pig pancreas-derived MOMs. Decellularized MOMs (12×12 mm) prepared from pig pancreas tissue as described in the Examples section which follows were seeded with fluorescent human MDA-MB-231/GFP breast carcinoma cells (green). FIGS. 15A-15B represent the cells (green) dispersed on the MOMs at day 1. FIGS. 15C-15D represent the cells (green) proliferating and populating the MOMs at day 7. FIGS. 15E-15F represent the cells (green) proliferating and populating all surfaces of the MOMs already at day 12 post seeding.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

DESCRIPTION OF SPECIFIC EMBODIMENTS OF THE INVENTION

The present invention is of devitalized, acellular micro-organ matrices for culture of cells, uses thereof for ex-vivo cell culture and tissue engineering. Specifically, the invention can be used for preparing cultured cells, for example, pancreatic islet cells, for transplantation into patients.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Although it is well known that organ-like architecture is critical for proper growth and function of cells, most ex-vivo cell culture remains limited to standard monolayer cultures. Attempts to develop three-dimensional scaffolds for cell culture not only lack the characteristic components and organization of natural stroma, but have also consistently encountered severe limitations in exchange of nutrients, gases and wastes, resulting in limited proliferation and loss of tissue specific function of the cultured cells, and reduced viability, function and engraftment after transplantation. This, along with the limited supply of organs and tissue for transplantation, has seriously impeded progress in transplantation medicine, for example, of islet cells for treatment of diabetes.

The instant inventors have previously demonstrated that micro-organs, organ fragments of microscopic thickness have been shown to remain viable, maintain the basic organ microstructure and transcribe tissue specific genes for long periods in culture. Micro-organs also function for long periods without vascularization when encapsulated and implanted into hosts. Devitalized, acellular scaffold matrices derived from micro-organs, termed micro-organ derived matrices (MOMs) have also been used for culturing and differentiating adult stem and progenitor cells.

Using the devitalized, acellular MOMs the present inventors have now surprisingly demonstrated that differentiated cells cultured on MOMs develop characteristic organ-specific spatial organization, proliferate robustly and can maintain functional competency for long periods of culture. As detailed in the Examples section that follows, lung AII-P progenitor cells seeded on acellular lung-derived MOMs quickly covered the scaffolds surfaces (FIGS. 2A-2C), creating alveolar structures, and expressed surfactants and other alveolar-specific proteins (FIGS. 1C, 1D, 2D and 3B), previously not observed in long term culture. Hepatocytes seeded on liver-derived MOMs expressed all liver-specific proteins assayed.

Pancreatic islets and islet cells cultured on pancreas-derived MOMs surprisingly maintained characteristic cellular organization (FIGS. 5A-5D), consistent proliferation (FIG. 5E), expressed beta-cell specific proteins (FIGS. 5G, 6A, 7A-7F) for up to 78 days in culture (FIG. 6B) and maintained glucose-responsive insulin secretion over long culture periods (FIG. 8). Most surprisingly, pancreatic islets cultured on non-homologous, lung-derived MOMs proliferated vigorously, developed islet-specific organization and maintained characteristic beta cell protein expression profiles which persisted throughout the long-term culture period (FIGS. 9A-9E, 10A-10H).

Thus, according to one aspect of some embodiments of the present invention, there is provided a composition of matter comprising a devitalized, acellular, tissue-derived three dimensional scaffold, said acellular three dimensional scaffold being of dimensions selected such that the point deepest within said scaffold is at least about 100 micrometers and not more than about 225 micrometers away from the nearest surface of the scaffold and differentiated cells seeded on said acellular three dimensional scaffold, wherein said differentiated cells are selected from the group comprising pancreatic islet cells, lung cells and hepatocytes.

As used herein, the terms "micro-organs", "MO", and "MOs" refer to at least one, preferably a plurality of, explants of tissue which retain the basic cell-cell, cell-matrix and cell-stroma architecture of the originating tissue.

Since the dimensions of the explant are important to the viability of the cells therein, if micro-organ functionality is to be sustained for prolonged periods of time (in-vivo, e.g., implanted or ex-vivo, e.g., cultured), the dimensions of the tissue explant are selected to provide diffusion of adequate nutrients and gases such as oxygen to every cell in the three dimensional micro-organ, as well as diffusion of cellular waste out of the explant so as to minimize cellular toxicity and concomitant death due to localization of the waste in the micro-organ. Thus, for example, cells positioned deepest within an individual micro-organ culture or explant are at least about 100 micrometers and not more than about 225 micrometers away from a nearest surface of the individual micro-organ culture, thereby in vivo architecture is preserved while at the same time it is ensured that no cell is farther than about 225 micrometers from the source of gases and nutrients. Preparation, culture and use of micro-organs is described in detail in U.S. Pat. No. 5,888,720, and PCT Applications No. IL03/00578, IL00/00365, IL00/00424 and U.S. 98/00594, all of which are incorporated herein by reference. In some embodiments, the micro-organs are prepared from organs excised under sterile conditions from freshly killed animals, kept on ice, rinsed with medium (e.g. Ringer or DMEM), and sectioned into 300 micrometer slices using a tissue chopper. In another embodiment, the micro-organs are prepared from fresh-frozen cryopreserved tissue or cryopreserved tissue sections, thawed to −2 to −10° C. for sectioning and sectioned, for example, using a pre-cooled tissue chopper or slicer.

Micro-organs suitable for preparation of the micro-organ matrices of the present invention can be prepared from any tissue (e.g., kidney tissue, liver tissue, lung tissue, skin tissue, pancreas tissue and gut derived tissue) from any animal, preferably a mammal, preferably a human. Further, in another embodiment, as tissue architecture, cell composition and extra-cellular matrix components often vary with the tissue, regions or specialized areas of the tissue may be selected for micro-organ preparation according to the intended use of the micro-organ matrix. For example, lobular lung tissue could be selected for lung-derived MOMs used for alveolar cell culture, the whole pancreas and preferably the "tail" of the pancreas may be selected for pancreas-derived MOMs used for islet cell culture.

The micro-organ matrices (MOMs) of the present invention are devitalized, acellular tissue-derived scaffolds prepared from micro-organ explants which have been treated to remove cells. As used herein, the term "scaffold" refers to a 3 dimensional matrix upon which cells may be cultured (i.e., survive and preferably proliferate for a predetermined time period).

As used herein, the terms "devitalized" and "acellular" refers to a tissue or structure from which all living, cellular mass has been removed. Devitalized, acellular micro-organs, for example, are micro-organ explants which no longer comprise any cells or other living matter, do not reproduce, do not require a supply of nutrients or gas, and are essentially inert. In some embodiments, cells are killed and then removed from the tissue, but cells can be removed without prior killing. Dead cells may be allowed to slough off in liquid, or may be chemically or mechanically removed. Methods for devitalization of tissue suitable for use with the present invention include thermal devitalization, irradiation, chemical stripping of cells by alkaline or acid treatment, hyperosmostic or hypo-osmotic devitalization, mechanical devitalization, detergents, organic solvents, combinations thereof and the like. It will be appreciated that inasmuch as the goal of devitalization is to provide an acellular scaffold for culture of cells, methods of devitalization suitable for use with the present invention are selected so as not to disrupt the structural and biochemical integrity of the acellular components of the micro-organ. Exemplary, but non-limiting methods for devitalization and removal of cells from micro-organs are detailed U.S. Pat. No. 7,297,540 and in the Materials and Methods of the Examples section that follows. In one exemplary method, micro-organs are treated with ammonium hydroxide and detergent (SDS) and washed thoroughly in saline to remove cellular mass. Alternatively, the micro-organs can be treated with 1-2 M NaCl and detergent (e.g. Triton, SDS, etc). In another embodiment, micro-organs from cryopreserved tissue are washed repeatedly and extensively in cold water, or in 1 M NaCl followed by detergent solution, finally washed and stored in water with or without preservative (e.g. antibiotics) before use. In yet another embodiment, the devitalized, acellular micro-organ matrices are stored frozen until use. Alternatively, the devitalized, acellular micro-organ matrices are dried (e.g. lyophilized), and rehydrated in water or medium before use.

As detailed in Example V that follows, the acellular micro-organ matrices of the present invention are characterized by a degree of tissue-specific biochemical composition. Peptide analysis of the acellular lung, liver and pancreas-derived MOMs uncovered a number of protein components common to MOMs from two or more tissue sources, such as collagen type XIV, laminin, clustrin and fibronectin, and other, tissue specific protein components such as integrin in liver MOMs and elastase in pancreatic MOMs. Further elucidation of the micro-organ matrix biochemical and spatial organization should afford opportunity to choose or engineer micro-organ matrices exquisitely suited for culture of specific cells, under highly specific conditions, for predetermined, specific functions. Thus, modified micro-organ matrices for use with the present invention are envisioned. Such modified MOMs can be, for example, MOMs derived from genetically modified animals, MOMs from micro-organ culture which have been genetically modified in-vitro or chemically modified MOMs. Genetically modified micro-organs are described in detail in PCT IL 01/00976, which is incorporated in its entirety herein.

The dimensions of the devitalized, acellular scaffolds of the present invention are selected such that the point deepest within said scaffold is at least about 100 micrometers and not more than about 225 micrometers away from the nearest surface of the scaffold. Thus, when populated with cells, the cells positioned deepest within the scaffold are at least about 100 micrometers and not more than about 225 micrometers away from the cells positioned at a nearest surface formed on the scaffold. In one embodiment, the scaffolds are devitalized, acellular tissue sections in the range of 100-450 micrometers thick. In another embodiment, the scaffolds are devitalized, acellular tissue sections about 300 micrometers thick. In yet another embodiment, the scaffolds are devitalized, acellular tissue sections about 300 micrometers thick and 12 mm wide by 12 mm long. In yet another embodiment, the scaffolds are devitalized, acellular tissue sections about 300 micrometers thick and at least 5, at least 10, at least 15, at least 20, at least 25, at least 30, at least 40, at least 50 mm in length, and at least 5, at least 10, at least 15, at least 20, at least 25, at least 30, at least 40, at least 50 mm in width.

Thus, according to one aspect of the present invention, there is provided a method of generating a composition of matter, the method comprising seeding differentiated cells on a devitalized, acellular, tissue-derived three dimensional scaffold, said acellular three dimensional scaffold being of dimensions selected such that the point deepest within said scaffold is at least about 100 micrometers and not more than about 225 micrometers away from the nearest surface of said scaffold, wherein said cells are selected from the group consisting of pancreatic islet cells, hepatic cells and alveolar cells.

As used herein, the phrase "differentiated cells" relates to cells which are committed in development to a certain cell type, and have lost totipotency. In some embodiments, the differentiated cells are terminally differentiated, e.g. have lost all ability to develop into cells of any other type, such as hepatocytes and pancreatic islet cells. In other embodiments, the cells are differentiated only partially, demonstrating characteristic morphology and cellular function, but retain some pluripotency, e.g. late progenitor cells. Differentiated cells suitable for culture on the micro-organ matrices of the present invention include cells collected from human and animal or commercially available cells.

The cell-types suitable for culture derived from various tissues, can be of human origin or that of any other mammal, and may be of any suitable source, such as a whole pancreas, parotid gland, thyroid gland, parathyroid gland, prostate gland, lachrymal gland, cartilage, kidney, lung, inner ear, liver, parathyroid gland, oral mucosa, sweat gland, hair follicle, adrenal cortex, urethra, and bladder, or portions or multiples thereof. In one embodiment, the cells are cells populating a solid organ, such as liver, kidney, pancreas, lung, and the like. In another embodiment, the cells are cells from hollow organs, for example bladder, stomach, and other visceral organs.

Use of differentiated mesenchymal stem cells from bone, cartilage, muscle, ligament, tendons, fat and stroma is envisioned. Directed differentiation can be employed to produce desired cell types, such as insulin producing cells (see, for example, Dong-Qi Tang, Diabetes 2004, vol 53; Sun Yu, et al. Chinese Medical Journal 2007, 120:771-76). Yet further, the use of embryonic stem cells and induced pluripotent cells to form differentiated cells, for example, islet cells, is envisioned (see, for example, Tateishi et al, J.Biol. Chem 2008; 283:31601-607; Zhang et al, Cell Res 2009; 19:429-38 and Jiang et al, Stem Cells 2007).

In yet another embodiment, cancerous cells (e.g. human MDA-MB-231/GFP breast carcinoma cells) can be cultured on the devitalized, acellular scaffolds of the invention.

The tissue cells can be prepared using any suitable method, such as by gently teasing apart the excised tissue or by digestion of excised tissue with collagenase via, for example, perfusion through a duct or simple incubation of, for example, teased tissue in a collagenase-containing buffer of suitable pH and tonic strength. The prepared tissue or cells then is concentrated using suitable methods and materials, such as centrifugation through density gradients for concentration (and partial purification). The concentrated tissue then is resuspended into any suitable vessel, such as tissue culture glassware or plasticware. The resuspended material may include whole substructures of the tissue, cells and clusters of cells. For example, such substructures may include whole islets and ducts in the case of pancreatic tissue and sinusoids in the case of liver tissue.

Tissue cells for use in the present invention can be cells freshly isolated from, live tissue soon after excising from a living animal, or cultured cells. As used herein, the term "live tissue" refers to tissue in which most of the cells are viable. In one embodiment, at least 50%, preferably 60%, more preferable 70%, more preferably 80%, more preferably 90% or 100% of the cells are viable in the "live" tissue. In one embodiment, seeding of the micro-organ matrices with freshly prepared cells can be effected within a range of about 5 minutes to about 2 hours of their removal from the tissue. In another embodiment, seeding is effected 1 hour, alternatively 50 minutes, alternatively 40 minutes, alternatively 30 minutes, alternatively 25 minutes, alternatively 20 minutes, alternatively 15 minutes and alternatively 10 minutes from removal from the tissue. In another embodiment, seeding is effected 10-15 minutes from removal from the tissue.

The initial culture of tissue cells is a primary culture. Methods and media for primary culture of mammalian cells are well known in the art. Cells can be cultured in monolayers, or, alternatively, the cells can be cultured cells from three dimensional cultures, for example, micro-organs, prepared and cultured as previously described (see supra). Basal media that may be used include those commercially available from Sigma Chemical Co., Life Technologies, Inc., or BioWhittaker Co. for example, DMEM, provided that medium components (ions, vitamins, nutrients) can be manipulated to a lower or higher concentration in the resultant medium.

According to one aspect of the present invention the cells are selected from pancreatic islet cells, lung cells and hepatocytes.

As used herein, the term "islet" or "islet of Langerhans" refers to a group of specialized cells in the pancreas that make and secrete hormones. An islet generally contains one or more of the following cell types: (1) alpha cells that make glucagon, which raises the level of glucose (sugar) in the blood; (2) beta cells that make insulin; (3) delta cells that make somatostatin which inhibits the release of numerous other hormones in the body; (4) pancreatic peptide producing PP cells; (5) D1 cells, which secrete vasoactive intestinal peptide; or (6) EC cells which secrete secretin, motilin, and substance P. Within the human pancreas organ there are about 1-1.5 million islets of Langerhans. The islets make up about 2% of the mass of the pancreas, and each islet contains between 2,000 and 10,000 cells.

As used herein, the term "islet cell" refers to any one of the cells found in an islet. In one embodiment, the islet cells used in the present invention are a combination of insulin-producing beta cells with other islet cell types.

In another embodiment, the islet cells consist of isolated beta cells. In yet another embodiment the islet cells consist of whole, isolated pancreatic islets of Langerhans. The islet cells can consist of cultured islets or islet cells, or non-cultured islet cells or islets. Cultured islets that proliferate while in culture are considered "expanded" islets. Thus, in yet another embodiment, the islet cells are cultured, expanded islet cells. In yet another embodiment, the islet cells are comprised in whole islets.

Methods of isolating islets are well known in the art (see, for example, Sharp et al, Transplantation, 1973; 16:686-89 and Stefan et al J Clin Inv. 1987; 80:175-83) For example, islets may be isolated from pancreatic tissue using collagenase and ficoll gradients. An exemplary method is described in Example 1 herein below. Briefly, the pancreas is cannulated and distended with cold enzyme (e.g. collagenase) solution (450 U/ml), the pancreas excised, and incubated at 37° C. for about 20-30 minutes. Following incubation, the islets are gently dislodged, washed in ice-cold medium (e.g. HBSS) plus 10% newborn calf serum, allowed to settle and the supernatant removed. The wash is repeated, and the washed digest passed through a 500 micron stainless steel screen and sedimented by centrifugation. The pellet is then mixed with Histopaque [1.110 gm/mL Histopaque (density=1.1085, Sigma Diagnostics Inc., St. Louis, Mo.)] and centrifuged. Islets floating on the gradient are collected and resedimented. Islets can also be picked under the stereoscope. Typically, the islets are isolated from mammals, preferably humans.

According to this aspect of the present invention, the islets may or may not be intact. Methods of dispersing islet cells include trypsinization or collagenase digestion (see Pralong et al, EMBO Journal, 1990; 9:53-56). Thus, the present invention also anticipates the use of tissue-engineered constructs comprising isolated beta cells or stem cells differentiated towards a beta cell lineage.

As used herein, the term "alveolar" or "lung alveolar" cell refers to cells derived from the lung alveolus. Alveolar cells include Type I "squamous alveolar cells", which form the alveolar wall, and Type II "great alveolar cells", which secrete surfactant. "Alveolar progenitor" cells are lung cells which are committed to differentiate into alveolar cells. AII-P progenitor cells are alveolar progenitor cells that differentiate into Type II alveolar cells.

Methods for isolating and culturing alveolar progenitor cells are well known in the art. For example, AII-P cells may be isolated by gently trypsinization of lung tissue and mechanical separation of the dissociate cells. Alveolar progenitor cells isolated thus can then be washed and seeded directly on micro-organ matrices of the present invention, or cultured in primary culture prior to seeding on the MOMs. One exemplary method of AII-P isolation and primary culture is described in detail in the Examples section that follows.

As used herein, the term "hepatocyte" refers to a liver parenchymal cell. Hepatocytes comprise most of the liver mass, and are involved in protein synthesis, protein storage and transformation of carbohydrates, synthesis of cholesterol, bile salts and phospholipids, and detoxification. Methods for hepatocyte isolation (for example, by collagenase) and culture are well known in the art. One exemplary method of hepatocyte isolation and primary culture is described in detail in the Examples section that follows.

Methods of seeding of the cells on scaffolds are well known in the art. Cells can be seeded in a scaffold by static loading, by seeding in stirred flask bioreactors, in a rotating wall vessel, or using direct perfusion of the cells in medium in a bioreactor. The cells may be seeded directly onto the micro-organ matrix scaffold, or alternatively, the cells may be mixed with a gel and absorbed onto the interior and exterior surfaces of the scaffold. An exemplary seeding procedure is described in the Examples section that follows.

The micro-organ matrix scaffolds seeded with the cells can be cultured in a culture medium. There are a large number of tissue culture media that exist for culturing cells from animals. Some of these are complex and some are simple. While it is expected that micro-organ cultures may grow in complex media, it has been shown here that the cultures can be maintained in a simple medium such as Dulbecco's Minimal Essential Media. Furthermore, the cultures may be grown in a media containing sera or other biological extracts such as pituitary extract. Moreover, the organ cultures can be maintained in the absence of serum for extended periods of time. In some embodiments of the invention, growth factors are not included in the medium during maintenance of the cultures in vitro.

The point regarding growth in minimal media is important. At present, most media or systems for prolonged growth of mammalian cells incorporate undefined proteins or use feeder cells to provide proteins necessary to sustain such growth. Because the presence of such undefined proteins can interfere with the intended end use of the subject micro-organ cultures, it may be desirable to culture the explants under conditions to minimize the presence of undefined proteins.

As used herein the language "minimal medium" refers to a chemically defined medium which includes only the nutrients that are required by the cells to survive and proliferate in culture. Typically, minimal medium is free of biological extracts, e.g., growth factors, serum, pituitary extract, or other substances which are not necessary to support the survival and proliferation of a cell population in culture. For example, minimal medium generally includes at least one amino acid, at least one vitamin, at least one salt, at least one antibiotic, at least one indicator, e.g., phenol red, used to determine hydrogen ion concentration, glucose, and other miscellaneous components necessary for the survival and proliferation of the cells. Minimal medium is serum-free. A variety of minimal media are commercially available from Gibco BRL, Gathersburg, MD, as minimal essential media.

However, while growth factors and regulatory factors need not be added to the media, the addition of such factors, or the inoculation of other specialized cells may be used to enhance, alter or modulate proliferation and cell maturation in the cultures. The growth and activity of cells in culture can be affected by a variety of growth factors such as insulin, growth hormone, somatomedins, colony stimulating factors, erythropoietin, epidermal growth factor, hepatic erythropoietic factor (hepatopoietin), and liver-cell growth factor. Other factors which regulate proliferation and/or differentiation include prostaglandins, interleukins, and naturally-occurring negative growth factors, fibroblast growth factors, and members of the transforming growth factor-β family.

The micro-organ cultures may be maintained in any suitable culture vessel such as 24 or 96 well microplates and may be maintained at 37° C. in 5% $CO_2$.

The cultures may be shaken for improved aeration, the speed of shaking being for example 12 rpm.

With respect to the culture vessel in/on which (optionally) the subject micro-organ cultures are provided, it is noted that in one embodiment such vessel may generally be of any material and/or shape. A number of different materials may be used to form the vessel, including but not limited to: nylon (polyamides), dacron (polyesters), polystyrene, polypropylene, polyacrylates, polyvinyl compounds (e.g., polyvinylchloride), polycarbonate (PVC), polytetrafluoroethylene (PTFE; teflon), thermanox (TPX), nitrocellulose, cotton, polyglycolic acid (PGA), cat gut sutures, cellulose, gelatin, dextran, etc. Any of these materials may be woven into a mesh. Where the micro-organ culture is itself to be implanted in vivo, it may be preferable to use biodegradable matrices such as poly glycolic acid, catgut suture material, or gelatin, for example. Where the cultures are to be maintained for long periods of time or cryopreserved, non-degradable materials such as nylon, dacron, polystyrene, polyacrylates, polyvinyls, teflons, cotton, etc. may be preferred. A convenient nylon mesh which could be used in accordance with the invention is Nitex, a nylon filtration mesh having an average pore size of 210 μm and an average nylon fiber diameter of 90 μm (#3-210/36, Tetko, Inc., N.Y.). Yet other embodiments are discussed below.

Cells can be seeded at different densities, for example, selected according to cell type and condition, micro-organ matrix type (tissue of origin) and culture conditions. In one embodiment, cells or tissue are seeded at about $1 \times 10^4$ to about $1 \times 10^6$ cells per micro-organ matrix. In another embodiment, cells are seeded at $2 \times 10^5$ to about $1 \times 10^6$ cells per 2-4 micro-organ matrices. In another embodiment, cells are seeded at $2 \times 10^5$ to about $1 \times 10^6$ cells per 5-7 micro-organ matrices. In one embodiment, cells are seeded in 24 well plates, in 1 ml of culture medium with 2 to 10 micro-organ matrices, and incubated at, for example, 37° C. in 5% $CO_2$, with changes of medium every two days.

In one embodiment, the composition of matter or engineered micro-organ comprises cells expressing at least one cell-specific protein after at least 7 days in culture. In another embodiment, the cells express the at least one cell-specific protein after at least 10, at least 15, at least 20, at least 30, at least 50 and alternatively at least 70 days in culture. In some embodiments, the seeded cells are beta cells and the cell-specific proteins are Pdx1, insulin and Glut2, secretion of insulin, amylin, C-peptide and/or glucagons. In yet another embodiment, the seeded cells are alveolar cells and the cell specific proteins are surfactant-C, surfactant-D, prosurfactant-B, aquaporin 5 or T1-α. In another embodiment, the seeded cells are hepatocytes and the cell specific proteins are albumin, Factor V, α-GST, GS or MUP.

Micro-organ matrices of a variety of origins can be used for culturing diverse cell types. Cells can be seeded on homologous tissue-derived scaffolds, or on non-homologous tissue-derived scaffolds. The inventors have surprisingly uncovered (see Example III that follows) that differentiated cells can be seeded and effectively cultured on non-homologous micro-organ matrices (MOMs derived from tissue other than that from which the cells have originated).

Example III shows, for the first time, pancreatic islets organizing in defined islet-specific spatial distribution on lung-derived micro-organ matrices, and maintaining robust proliferation and cell-specific protein (e.g. surfactant) expression throughout intermediate and long term culture. Thus, in another embodiment, the endocrine cells are pancreatic islet cells and the scaffold is a lung-derived scaffold. Seeding and culturing of pancreatic islet cells on micro-organ matrices derived from other tissue is also envisioned.

Cells seeded on micro-organ matrices of the invention thrive, proliferate and function in culture. Thus, according to one aspect of the present invention there is provided an engineered micro-organ comprising a devitalized, acellular, tissue-derived three dimensional scaffold, said acellular three dimensional scaffold being of dimensions selected such that the point deepest within said scaffold is at least about 100 micrometers and not more than about 225 micrometers away from the nearest surface of the scaffold; and differentiated cells seeded on said acellular three dimensional scaffold.

As used herein, the term "engineered micro-organ" or "artificial micro-organ" refers to a micro-organ scaffold seeded with differentiated cells having a tissue-specific function when cultured and, optionally organized in a micro-organ-like three dimensional tissue structure. The tissue type and function of such an engineered micro-organ can be determined by the (i) conditions of culturing; (ii) body tissue type into which the seeded scaffold is implanted; (iii) micro-organ tissue from which the scaffold was generated and/or (iv) type of cells seeded on the scaffold.

Thus, according to one aspect of the present invention, there is provided a method of generating an "engineered micro-organ" the method comprising seeding cells on a devitalized, acellular, tissue-derived three dimensional scaffold, said acellular three dimensional scaffold being of dimensions selected such that the point deepest within said scaffold is at least about 100 micrometers and not more than about 225 micrometers away from the nearest surface of said scaffold, wherein said cells are selected from the group consisting of pancreatic islet cells, hepatic cells and alveolar cells.

Thus, according to one embodiment, the engineered micro-organ comprises a scaffold seeded with pancreatic islet cells. In one embodiment, the scaffold is seeded with dissociated pancreatic islet cells. In another embodiment, intact pancreatic islets are seeded onto the scaffold. In one embodiment, the scaffold is a pancreas-derived acellular micro-organ matrix. In another embodiment, the scaffold is a lung-derived acellular micro-organ matrix.

As detailed in Examples II and III that follow, the islet cells of such an engineered pancreatic micro-organ can organize and function in an islet-specific manner, throughout long term cell culture. According to one embodiment, characteristic islet cell function includes, but is not limited to expression of Pdx1, insulin and Glut2, secretion of insulin, amylin, C-peptide and/or glucagon, electrical activity, and glucose-responsive insulin secretion. Methods for monitoring islet specific protein expression include, but are not limited to RT-PCR for transcription of relevant genes, immunohistochemistry and quantitative immunodetection techniques such as ELISA.

Glucose responsive insulin secretion can be determined by the change in insulin secretion of islets or islet-MOM cultures when the concentration of glucose in the medium is raised from "low glucose" to "high glucose" levels, as described by Marchetti et al (Diabetes, 1994; 43:827-30). Such a protocol, using 3 mM glucose as the low levels, and 16.7 mM glucose as the high levels, is currently standard procedure for testing isolated islet function before transplantation.

Exemplary methods, antibodies, PCR primers and the like for monitoring islet cell function and organization in culture are detailed in the Examples section that follows.

Thus, according to some embodiments, insulin secretion of the pancreatic beta cells increases at least two fold when said micro-organ is first exposed to about 3 mM glucose and then exposed to about 16.7 mM glucose. In some embodiments, pancreatic islet cells of engineered micro organ are characterized by glucose responsive insulin secretion after at least 7 days in culture, alternatively at least 10 days in culture, alternatively at least 14 days in culture, alternatively at least 20 days in culture, alternatively at least 24 days in culture, alternatively at least 28 days in culture, alternatively at least 35 days in culture, alternatively at least 40 days in culture, alternatively at least 50 days in culture, alternatively at least 60 days in culture, alternatively at least 70 days in culture and alternatively at least 78 days in culture. In some other embodiments, the islet cells express Glut2 or Pdx1 following at least 7 days in culture, alternatively at least 14 days in culture, alternatively at least 20 days in culture, alternatively at least 28 days in culture and alternatively at least 35 days in culture.

According to yet another aspect of the present invention there is provided an engineered micro-organ comprising a devitalized, acellular tissue-derived three dimensional scaffold seeded with lung alveolar cells. In one embodiment, the scaffold is seeded with freshly prepared AII-P cells. In another embodiment, cultured AII-P cells are seeded onto the scaffold. In one embodiment, the scaffold is a liver-derived acellular micro-organ matrix. In another embodiment, the scaffold is a lung-derived acellular micro-organ matrix.

According to one embodiment, characteristic alveolar cell function includes, but is not limited to expression of surfactant-C, surfactant-D, prosurfactant-B, aquaporin 5 and T1-α. Methods for monitoring alveolar specific protein expression include, but are not limited to RT-PCR for transcription of relevant genes, immunohistochemistry and quantitative immunodetection techniques such as ELISA. Exemplary methods, antibodies, PCR primers and the like for monitoring alveolar cell function and organization in culture are detailed in the Examples section that follows.

Thus, according to some embodiments, alveolar cells of engineered micro organs are characterized by surfactant-C secretion after at least 5 days in culture, alternatively at least 8 days in culture, alternatively at least 14 days in culture, alternatively at least 21 days in culture, alternatively at least 30 days in culture, alternatively at least 40 days in culture, alternatively at least 50 days in culture and alternatively at least 70 days in culture. In some other embodiments, the alveolar cells express surfactant-D, prosurfactant-B, aquaporin 5 and T1-α following at least 8 days in culture, alternatively at least 14 days in culture, alternatively at least 20 days in culture, alternatively at least 28 days in culture and alternatively at least 35 days in culture. In one embodiment, the scaffold is a devitalized, acellular liver-derived scaffold, and the alveolar cells express T1-α following at least 8 days in culture.

According to yet another aspect of the present invention there is provided an engineered micro-organ comprising a devitalized, acellular tissue-derived three dimensional scaffold seeded with hepatocytes. In one embodiment, the scaffold is seeded with freshly prepared hepatocytes cells. In another embodiment, cultured hepatocytes are seeded onto the scaffold. In one embodiment, the scaffold is a liver-derived acellular micro-organ matrix.

According to one embodiment, characteristic liver cell function includes, but is not limited to expression of at least one liver specific protein selected from the group consisting of albumin, Factor V, α-GST, GS and MUP. Methods for monitoring liver specific protein expression include, but are not limited to RT-PCR for transcription of relevant genes, immunohistochemistry and quantitative immunodetection techniques such as ELISA. Exemplary methods, antibodies, PCR primers and the like for monitoring alveolar cell function and organization in culture are detailed in the Examples section that follows.

Thus, according to some embodiments, alveolar cells of engineered micro organs are characterized by expression of at least one of albumin, Factor V, α-GST, GS and MUP after at least 5 days in culture, alternatively at least 8 days in culture, alternatively at least 14 days in culture, alternatively at least 21 days in culture, alternatively at least 30 days in culture, alternatively at least 40 days in culture, alternatively at least 50 days in culture and alternatively at least 70 days in culture. In one embodiment, the scaffold is a devitalized, acellular lung-derived scaffold, and the alveolar cells express Factor V following at least 8 days in culture.

Since the compositions and micro-organs of the present invention comprise cells that are capable of storing and secreting cell-specific proteins, such as alveolar cells secreting surfactant, and islet cells secreting insulin, they may be used for treating diseases which is associated with cell-specific protein deficiency such as lung disease or diabetes.

Thus, according to another aspect of the present invention there is provided a method of treating diabetes in a subject, the method comprising transplanting a therapeutically effective amount of an engineered micro-organ comprising pancreatic islet cells seeded on a devitalized, acellular micro-organ matrix of the present invention into the subject, thereby treating diabetes.

As used herein "diabetes" refers to a disease resulting either from an absolute deficiency of insulin (type 1 diabetes) due to a defect in the biosynthesis or production of insulin, or a relative deficiency of insulin in the presence of insulin resistance (type 2 diabetes), i.e., impaired insulin action, in an organism. The diabetic patient thus has absolute or relative insulin deficiency, and displays, among other symptoms and signs, elevated blood glucose concentration, presence of glucose in the urine and excessive discharge of urine.

Thus, according to another aspect of the present invention there is provided a method of treating an alveolar lung disease in a subject, the method comprising transplanting a therapeutically effective amount of an engineered micro-organ comprising alveolar cells seeded on a devitalized, acellular micro-organ matrix of the present invention into the subject, thereby treating said alveolar lung disease. Alveolar lung disease is associated with pulmonary edema (cardiogenic or neurogenic), pneumonia (bacterial or viral), pulmonary embolism, systemic lupus erythemosus, pulmonary hemorrhage), idiopathic pulmonary haemosiderosis, and Wegner granulomatosis, PAP, alveolar cell carcinoma, and other conditions. The use of the engineered micro-organ comprising alveolar cells for surfactant replacement therapy is also contemplated.

The phrase "treating" refers to inhibiting or arresting the development of a disease, disorder or condition and/or causing the reduction, remission, or regression of a disease, disorder or condition in an individual suffering from, or diagnosed with, the disease, disorder or condition. Those of skill in the art will be aware of various methodologies and assays which can be used to assess the development of a disease, disorder or condition, and similarly, various methodologies and assays which can be used to assess the reduction, remission or regression of a disease, disorder or condition.

As used herein, "transplanting" refers to providing the engineered micro-organ of the present invention, using any suitable route. Typically, the pancreatic or liver micro-organ may be administered by injection using a catheter into the portal vein of the liver, underneath the kidney capsule, although other methods of administration are envisaged. For example, Dufour et al., [Tissue engineering, September 2005, Vol. 11, No. 9-10: 1323-1331] successfully administered scaffold supported islet cells in the epididymal fat pad of diabetic mice. It will be appreciated that more than 1 micro-organ can be transplanted at the same time to the same individual. Dosage and character of the micro-organs for transplantation can be determined by the attending physician as needed, for example, according to the severity of the disease.

In one embodiment, the micro-organs are transplanted within the subject soon after seeding. Alternatively, the seeded cells can be cultured for hours, days or weeks before transplantation. In one embodiment, the micro-organ matrices are cultured for about 5 minutes to about 2 hours after seeding. In another embodiment, transplanting is effected 10 hours, alternatively 24 hours, alternatively 2 days, alternatively 7 days, alternatively 10 days, alternatively 14 days, alternatively 28 days and alternatively 70 days after seeding.

Any of the islet or alveolar cells of the present invention can be derived from either autologous sources or from allogeneic sources such as human cadavers or donors. Since non-autologous cells are likely to induce an immune reaction when administered to the body several approaches have been developed to reduce the likelihood of rejection of non-autologous cells. These include either suppressing the recipient immune system or encapsulating the non-autologous cells in immunoisolating, semipermeable membranes before transplantation.

Examples of immunosuppressive agents include, but are not limited to, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE.sup.R), etanercept, TNF.alpha. blockers, a biological agent that targets an inflammatory cytokine, and Non-Steroidal Anti-Inflammatory Drug (NSAIDs). Examples of NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors and tramadol.

It will be noted that, within islet transplantation perspective, islet cells cultured on organ-derived acellular scaffolds provide a significantly weaker—if at all—immunological challenge, compared to that of transplanted allogeneic islets. Furthermore, the engineered tissues could be encapsulated in order to allow heterologous implantations. Encapsulation techniques are generally classified as microencapsulation, involving small spherical vehicles and macroencapsulation, involving larger flat-sheet and hollow-fiber membranes (Uludag, H. et al. Technology of mammalian cell encapsulation. Adv Drug Deliv Rev. 2000; 42: 29-64). This could be achieved by many methods of encapsulation known in the art or, as a way of exemplification they could be encapsulated into a sealed planar polycarbonate capsule. Specific methods for encapsulation of micro-organs are detailed in WO04078916 and U.S. Pat. No. 6,472,200, which are incorporated herein by reference. When such encapsulated tissues are implanted for example into a xenogenic host, the implanted tissue secretes angiogenic factors which induce the formation of a vascular network surrounding the capsule. In such circumstances the tissue inside the capsule receives nutrients and gases by diffusion through the membrane and remains viable for very long periods. An exemplary method for transplantation of engineered micro-organs is provided in the Examples section which follows.

The compositions and engineered micro-organs of the present invention may be transplanted to a human subject per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the compositions and engineered micro-organs of the present invention accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer.

Pharmaceutical compositions suitable for use in context of the present invention include compositions wherein the active ingredients are contained in an amount effective to achieve the intended purpose. More specifically, a therapeutically effective amount means an amount of active ingredients (compositions and engineered micro-organs) effective to prevent, alleviate or ameliorate symptoms of a disorder (e.g. diabetes or a lung disease) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated from animal models (e.g. STZ diabetic mice) to achieve a desired concentration or titer. Such information can be used to more accurately determine useful doses in humans.

Toxicity and therapeutic efficacy of the active ingredients described herein can be determined by standard pharmaceutical procedures in experimental animals. The data obtained from these animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p1).

Dosage amount and interval may be adjusted individually to provide cell numbers sufficient to induce normoglycemia (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

Since the compositions and micro-organs of the present invention comprise cells that are capable of storing and secreting cell-specific proteins, such as alveolar cells secreting surfactant, hepatocytes expressing albumin, Factor V, etc and islet cells secreting insulin, they may be used for producing cell specific proteins in-vitro.

Thus, according to another aspect of the present invention, there is provided a method of producing a cell specific protein comprising in-vitro culturing the engineered micro-organ under conditions which promote cell growth and proliferation, and isolating said cell-specific protein from said culture.

In some embodiments, the engineered micro-organ is seeded with pancreatic islet cells, and the cell specific protein is selected from the group consisting of insulin, Pdx1 and Glut2.

In some embodiments, the engineered micro-organ is seeded with alveolar cells, and the cell specific protein is selected from the group consisting of surfactant-D, surfactant-C, prosurfactant-B, aquaporin 5 and T1-α.

In some embodiments, the engineered micro-organ is seeded with hepatocytes, and the cell specific protein is selected from the group consisting of albumin, Factor V, alpha-glutathione-s-transferase (α-GST), glycogen synthase (GS) and major urinary protein (MUP).

Methods for detecting and isolating the cell specific proteins are well known in the art, for example, gel chromatography, size filtration, dialysis and the like.

In some embodiments, the culturing is for at least 7 days in culture, alternatively at least 10 days in culture, alternatively at least 14 days in culture, alternatively at least 20 days in culture, alternatively at least 24 days in culture, alternatively at least 28 days in culture, alternatively at least 35 days in culture, alternatively at least 40 days in culture, alternatively at least 50 days in culture, alternatively at least 60 days in culture, alternatively at least 70 days in culture and alternatively at least 78 days in culture.

As used herein the term "about" refers to ±10%.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Experimental Methods

Preparation of Micro-Organs

Micro-organs (MOs) were prepared from organs (e.g. lung, pancreas or liver) of mice or pigs as described hereinabove and in U.S. Pat. Nos. 7,297,540; 5,888,720, and PCT Applications No. IL00/00365, IL00/00424 and US98/

00594. Adult animals were sacrificed by asphyxiation with $CO_2$ and the respective organs removed under sterile conditions. Organs were kept on ice and rinsed once with Ringer solution or DMEM (Beit Haemek, Israel) including 4.5 gr/liter D-glucose and thereafter using a Sorvall tissue chopper, cut into 300 μm slices to form MOs. The MOs were washed again (2-3 times) as above and incubated in DMEM containing 100 units per ml penicillin, 1 mg/ml streptomycin and 2 mM L-glutamine (Beit Haemek, Israel), 5% $CO_2$ atmosphere, 37° C. Incubation medium was change every 1-2 days.

Preparation of "Devitalized" Three-Dimensional Scaffolds (Micro-Organ Matrices "MOM"s) from Micro-Organs MOs are prepared as described herein and are treated for 5 minutes with 0.67% ammonium hydroxide in 0.5% SDS. After all of the cellular mass is removed the remaining extracellular (devitalized acellular) mass is washed thoroughly in five changes of PBS, after which the matrix is ready for use as a three-dimensional scaffold. Cells can then be plated onto the MOM and cultured for any desired time period. Optionally, the MOMs can be frozen at −70° C. until required, thawed and washed 3 times in PBS and 2 times in culture media prior to using in culture.

Alternatively, MOs prepared as described herein are immersed in one of (a) 10-50 mM $NH_4OH$+0.2-3% TritonX-100; (b) 1-2M NaCl; (c) 1-2M NaCl+0.2-3% Triton X-100; or (d) 1-2M NaCl+0.01-0.1% SDS, for a period of 45 min. The resulting MOMs then undergo 5×15 min washes in sterile distilled $H_2O$. At this stage the resulting MOMs can be stored frozen at −80 C. or rinsed in 5×15 min washes in PBS prior to using.

Alternatively, the organ is excised fresh, washed in water, cleaned and optionally stored on ice for up to 1.5 hours. Prior to slicing, the organ is cut into columns 12 mm×12×20-40 mm and frozen at −20° C. to −80 C and kept frozen until required for MOM preparation. Prior to cutting the organ columns are equilibrated to −2° to −10° C. and then sliced into 200 to 500 um×12×12 mm sections using a pre-cooled tissue slicer.

MOMs can then be prepared from the cut sections as follows:

I: a. Cut sections are washed in cold sterile DDW for a 1 hour, with water changes every 15 minutes (approximately 50 ml of DDW for each wash);
 b. Cut sections are washed in room temperature (r.t.) sterile DDW for an additional 4 hours, with water changes every 20 minutes (approximately 50 ml of DDW for each wash); and
 c. Cut sections are stored at −80° C. in minimal volume of DDW until required for seeding.

Or alternatively:
II: a. Cut sections are washed in room temperature sterile DDW for an additional 4 hours, with water changes every 20 minutes (approximately 50 ml of DDW for each wash); and
 b. Cut sections are kept overnight at 4° in DDW.
 C. Cut sections are then stored at −80° C. in minimal volume of DDW until required for seeding.

Or alternatively:
III: a. Cut sections are washed in room temperature sterile DDW for an additional 4 hours, with water changes every 20 minutes (approximately 50 ml of DDW for each wash); and
 b. Cut sections are kept overnight at 4° in DDW.
 C. Cut sections are stored in PBS in 10× antibiotic for 1 to 10 days prior to seeding cells on the resulting MOMs.

Or alternatively:
IV: a. Cut sections are placed in 1M NaCl for 1 hour, with 3 changes, every 20 min;
 b. Cut sections are transferred to a solution of 0.5% Triton in $H_2O$ for 3 hours and changed every 30 minutes;
 c. Cut sections are washed with $H_2O$ 3×15 min each: and
 d. Cut sections are stored in PBS in 10× antibiotic for 1 to 10 days prior to seeding cells on the resulting MOMs.

Or alternatively:
V: a. Cut sections are placed in 1M NaCl for 1 hour, with 3 changes, every 20 min;
 b. Cut sections are transferred to a solution of 0.5% Triton in $H_2O$ for 3 hours and changed every 30 minutes;
 c. Cut sections are washed with $H_2O$ 5×15 min each: and
 d. Cut sections are then stored at −80° C. in minimal volume of DDW until required for seeding.

Transgenic Pdx-1-GFP Mice

Transgenic mice expressing the green fluorescent protein (GFP) gene under transcriptional control of the pancreas-specific gene Pdx1 were developed by Gu et al (Development, 2004).

MOMs Implantation

Adult C-57 mice were anesthetized using 0.6 mg Sodium Pentobarbital per gram body weight. The mice were shaved, and an incision about 2 cm long was made in the skin at an area above the stomach. A hemostat was used to create a subcutaneous "pocket" at the side of the incision, and 2-6 MOs were implanted inside the pocket. Implantation was done by simply layering the MOs over the muscle layer. The incision was sutured and the animals were kept in a warm, lit room for several hours following which they were transferred to the animal house. Animals were sacrificed at different time interval following implantation and the implanted MOs were examined under a surgical microscope.

Isolation and Culture of AII-P Cells

Lungs were dissected from 4-5 week old C57BL/6 mice. The tissue was cut into small pieces and then digested using 0.25% trypsin-0.05% EDTA solution for 30-40 min at 37° C. and gently pipetted to mechanically separate cells. The cells were collected by centrifugation and re-suspended in culture medium (DMEM containing 10% fetal calf serum, 100 U/ml penicillin, 1 mg/ml streptomycin and 2 mM L-glutamine (Beit Haemek, Israel)). The cell suspension was seeded in culture medium at a cell density of 300,000 cells/cm² and cultured at 37° C. in 5% $CO_2$. After 24 hours, the non-adherent cells were removed by replacing the medium and leaving only the adherent type II cells (3). The medium was replaced every 2-3 days until the cells reached confluency (approximately 5-7 days). Confluent cells were removed and used to seed the MOMs.

Isolation of Hepatocytes

Hepatocytes were isolated by collagenase perfusion following the method described by Selgen. Briefly, after two step perfusion of the whole animal with calcium-free buffer and collagenase, cells were dissociated, and collected by centrifugation. The cells were then suspended and cultured with hepatocyte culture medium (HCM, Cambrex).

Co-Culture of Cells with MOMs

Cells or tissue was seeded on lung-derived MOMs or liver-derived MOMs and cultured at a density of 5-7 lung-derived MOMs per well or 2-4 liver-derived MOMs per well in 24 well plates in 1 ml of culture medium. Cell concentration varied from $2 \times 10^5$ to $10^6$ cells per ml per well. After 24 hours, the seeded MOMs were transferred to new wells in order to eliminate non-adherent cells. The medium was changed every 2 days. Incubation took place at 37° C. in 5% $CO_2$.

Cryostat Sections.

MOMs were fixed for 15 min in phosphate buffered saline containing 4% para formaldehyde, rinsed, and embedded in TissueTek (Sakura, Japan). 8 μm thick cryo-sections were prepared and nuclei were stained with 10 μg/ml 4,6-diamino-2-phenylindole dihydrochloride (DAPI, Sigma) for visualization of cell nuclei.

Transmission Electron Microscopy

MOMs samples were fixed in 1% formaldehyde 2.5% gluteraldehyde, postfixed in 1% osmium tetroxide, dehydrated and embedded in Epon using standard techniques. Ultra thin sections (60-80 nm thick) were prepared using an Ultratome III (LKB). The sections were collected on 200 mesh thinbar grids and counterstained with uranyl acetate and lead-citrate and examined using a Philips CM 120 transmission electron microscope.

Isolation and culture of mouse pancreatic islets: Adult pancreatic islets were isolated from mice pancreases by using collagenase P (Roche). Briefly, the bile duct was clamped off at its duodenal insertion by using a small bulldog clamp. A total of 5 ml 1.5 mg/ml collagenase was injected into the bile duct until the pancreas swelled. The pancreas was excised, followed by digestion at 37° C. for 15 min. in medium containing antibiotics (100 μg/ml penicillin G and 100 μg/ml of streptomycin), and no additional collagenase. The digest was washed in cold medium. After two centrifugations, islets were handpicked under a stereomicroscope.

Islets or islet cells were then cultured in culture medium at 37° C. in an incubator supplemented with 5% CO and 95% air.

Isolation and Propagation of Embryonic Stem Cells (ESCs)

Cell culture: CCE ESCs (Levinson-Dushnik and Benvenisty, 1997) were maintained in Dulbecco's modified Eagle medium (DMEM) supplemented with 15% heat inactivated fetal calf serum (HI-FCS), 100 units per ml penicillin, 1 mg/ml streptomycin, 2 mM L-glutamine, nonessential amino acid solution (Beit Haemek, Israel), 70 μM β-mercaptoethanol and 1,000 units per ml leukemia inhibitory factor (LIF) (Gibco BRL) on mitomycin treated STO cells or on gelatin-coated tissue culture plates. The growth medium was changed every day.

When grown over a non-adhesive plastic, ESCs differentiate and aggregate to form a colony known as embryoid body (EB) (Keller, 1995). At day 3 EBs start to show an outer endodermal layer and inner ectodermal layer (Abe et al., 1996). The EBs used in the experiments described herein were 3 days old. CCE EBs were also grown over non-adhesive plastic petri dish under the same conditions without the addition of LIF; the growth medium was replaced every day.

Immunohistochemistry: MOs were fixed in a fixation solution containing 0.05 M sodium phosphate buffer (i.e., 0.04 M $Na_2HPO_4$ and 0.011 M $NaH_2PO_4$, pH 7.4), 0.2% gluteraldehyde, 2% formaldehyde and 2 mM $MgCl_2$. Following fixation, the MOs were washed three times with a washing solution containing 0.05 M sodium phosphate buffer, 2 mM $MgCl_2$ and 0.02% NP40. MOs were incubated overnight with primary antibodies (primary rabbit antibodies to pre-surfactant protein B (Chemicon), insulin, Glut2, Ki67, surfactant-C, GFP and Pdx1, diluted 1:800), washed with 0.5% Triton/PBS and incubated for two hours with a secondary antibody. Cy3-conjugated goat anti-rabbit (Jackson ImmunoResearch Labs), diluted 1:800, was used for immuno-fluoresence while peroxidase-conjugated goat anti-rabbit (Jackson ImmunoResearch Labs), diluted 1:1000 was used for immuno-histochemistry. Alternatively, the primary antibodies were fluorescent labeled, and no secondary antibodies were required for detection. Washing was repeated and sections were counter stained respectively with 10 μg/ml DAPI (Sigma) or with hematoxylin and washed again. Sections were mounted under coverslips and viewed with conventional fluorescence or light microscopy.

RNA isolation: Cells were collected from either the culture medium, the culture dish surface or dissected from MOs surface by micropipetting. Total RNA was extracted from tissues or cell with acid-guanidine and phenol using the Chomczynski method (Chomczynski, 1994). RNA was separated on a 1% agarose gel to assess both quantity and quality.

Reverse transcription (RT) PCR: cDNA was synthesized from 1-2 μg total RNA using poly $d(T)_{12-18}$ (Pharmacia Bio-tech) primer and Moloney murine leukemia virus reverse transcriptase (Promega). Two μl cDNA samples were subjected to PCR amplification using Taq DNA polymerase (Promega) in 1.5 mM $MgCl_2$ (37 cycles). The PCR primers used, the fragment sizes and annealing temperatures used for each pair of primers are summarized in Table 1 below:

TABLE 1

| Gene | Forward primer(SEQ ID NO.) | Reverse primer(SEQ ID NO.) | AT* (° C.) | Product length (bp) |
|---|---|---|---|---|
| β-actin | TACCACAGGCATTGTGATGG(1) | AATAGTGATGACCTGGCCGT(2) | 55 | 310 |
| SP-C | ACACCATCGCTACCTTTTCC(3) | CTTTCCTTTACAGACTTCCACC(4) | 57 | 435 |
| SP-D | TTGCCTTCTCCCACTATCAG(5) | GCCTTATCATTCCATTGCCC(6) | 56 | 364 |
| CC10 | TCATGCTGTCCATCTGCTGC(7) | AAAGAGGAAGGAGGGGTTCG(8) | 55.8 | 343 |
| AQP-5 | TGAAGAAGGAGGTGTGTTCAG(9) | TGGTGTTGTGTTGTTGCTG(10) | 58 | 381 |
| T1α | TGAATCTACTGGCAAGGCAC(11) | ACAGGAAGAGGATGGGGAAC(12) | 55.4 | 424 |
| Albumin | AACACAAAGATGACAACCCC(13) | CCAATGCTTTCTCCTTCACAC(14) | 54.2 | 261 |
| Factor V | GACAACCCCAGCATCAAAC(15) | TAGAAGCAGCCCTATCAGCC(16) | 55.3 | 345 |

TABLE 1-continued

| Gene | Forward primer(SEQ ID NO.) | Reverse primer(SEQ ID NO.) | AT* (° C.) | Product length (bp) |
|---|---|---|---|---|
| GS | AGCTGAATGCACAGTGATGG(17) | GAAAAGCCCTGCTCAGTGTC(18) | 60 | 305 |
| α-GST | GGCGGATCTGGAGATAATGA(19) | CATCAAAAGGCTTCCTCTGG(20) | 60 | 329 |
| MUP | TGTGTCCATGCAGAAGAAGC(21) | GGAAGGTTTCCCCATCATTT(22) | 60 | 335 |

*AT - Annealing temperature

PCR products were separated in a 2% agarose gel in the presence of ethidium bromide. Gels were photographed and analyzed densitometrically using the NIH image version.

Example I

Alveolar Structures from AII-P Lung Progenitors Grown on MOMs

AII-P Lung alveolar progenitors do not typically retain lung-specific gene expression when grown in long-term primary culture, and gradually lose the ability to express surfactant protein after several passages. The ability of devitalized, acellular micro-organ matrices (MOMs) to support growth and tissue-specific function of lung progenitors was tested by seeding primary lung progenitors on lung-derived MOMs.

Figure 1A:
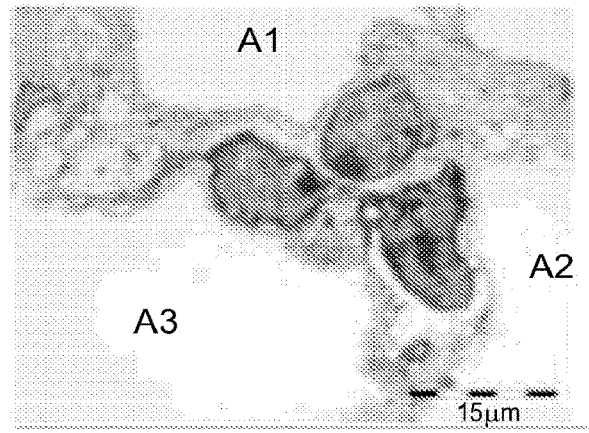
FIGS. 1A-1D are microscope images showing alveolar organization and lung-specific function of lung progenitor AII-P cells seeded onto lung-derived, cell-free micro-organ matrices (MOMs).
Figure 1B:
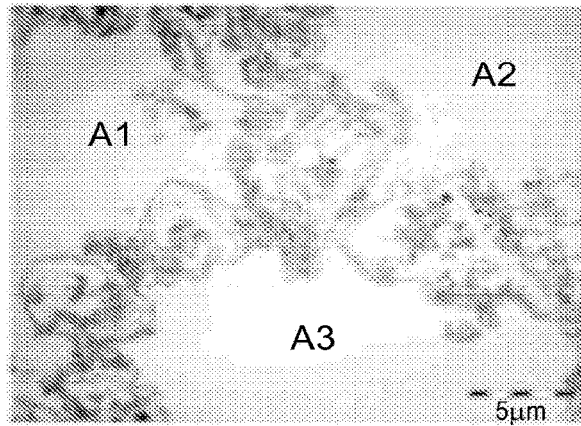
Figure 1C:
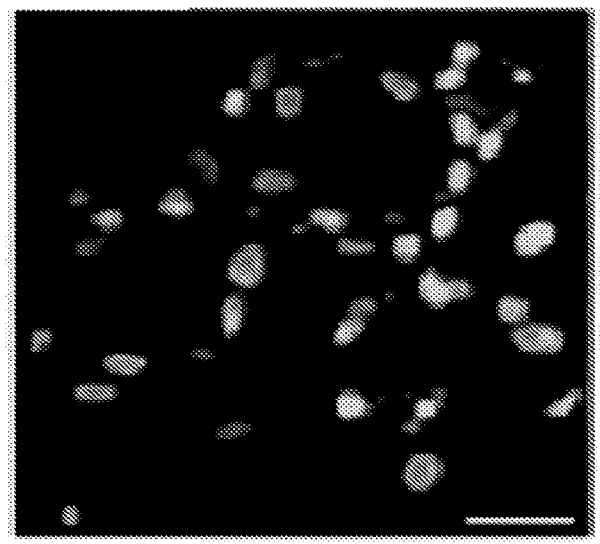
Figure 1D:
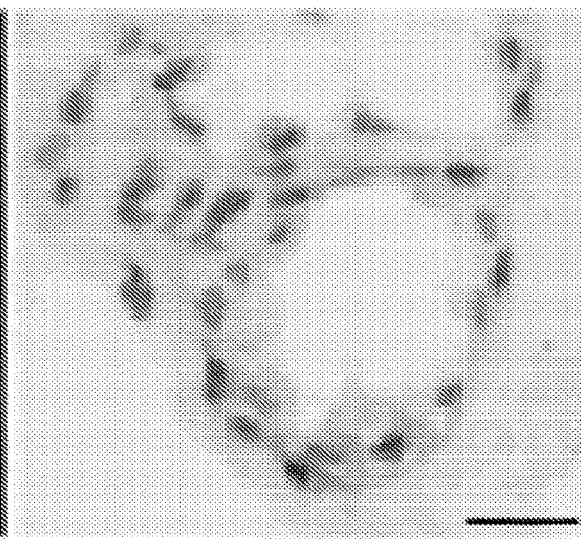

When adult mouse AII-P lung progenitor cells were seeded onto lung-derived MOMs, they proliferated and organized into alveolar structures, similar to normal lung alveoli in both morphology and function. Inspection of transmission electron micrographs of normal lung tissue (FIG. 1A) compared with primary lung progenitors grown on MOMs (FIG. 1B) reveals characteristic alveolar spaces (A1-A3) separated by septal walls in both preparations. Microscopic examination of sectioned AII-P lung-progenitor-lung MOM cultures formation of an epithelium, which by 27 days in culture (FIG. 1C) had lined the entire matrix including all alveolar cavities (bar=50 um). Staining for surfactant-B protein (FIG. 1C, red color) revealed surfactant-B expression in about 30% of the cells lining each alveolus. When viewed under higher magnification, a hematoxylin and eosin stained 27 day section further reacted with anti-surfactant-B antibodies (FIG. 1D, brown color) of the culture revealed the remarkably natural alveolar structure formed, indistinguishable from a natural alveolus. Further, the AII-P lung progenitor-lung MOM cultures maintain characteristic spatial expression of surfactant-B: within each alveolus formed, a heterogeneous spatial pattern of expression of the surfactant-B gene similar to the in vivo situation is observed (bar=30 um). These results reveal that adult lung-derived MOMs can be a reliable way to create or maintain patterns of both structural and functional organization. Without wishing to be restricted to a single hypothesis, one interpretation of the results is that MOMs, and specifically lung-derived MOMs can provide instructive signals which may be highly localized.

Figure 2A:
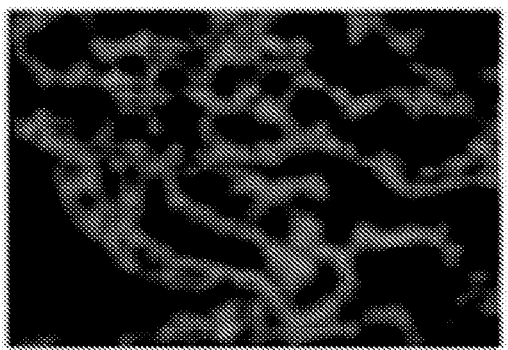
FIGS. 2A-2D are microscope images showing alveolar organization and lung-specific function of AII-P lung progenitor cells seeded onto lung-derived cell-free micro-organ matrices (MOMs).
Figure 2B:
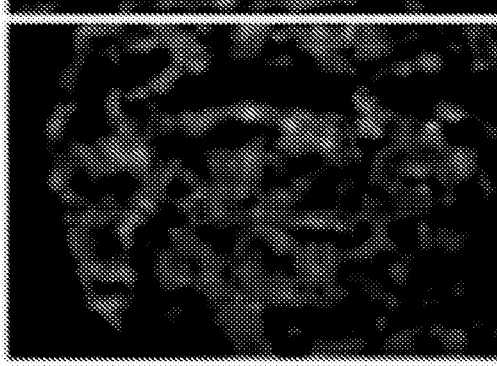
Figure 2C:
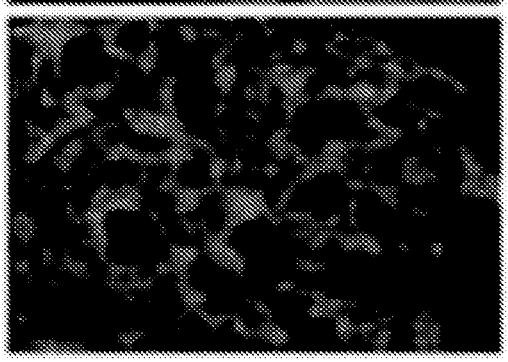
Figure 2D:
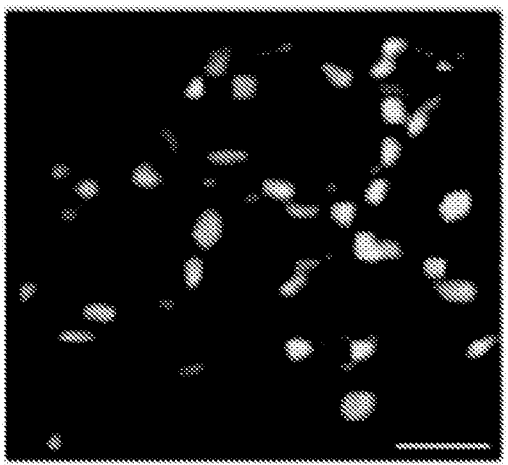

In order to follow the dynamics of lung-progenitor-lung MOM growth in culture, AII-P lung-progenitor-lung MOMs were sectioned and examined at various times following initiation. FIGS. 2A-2C reveal gradual proliferation (FIG. 2A=initiation of culture, day 0; FIG. 2B=8 days culture, FIG. 2C=21 days culture) over the entire surfaces of the lung-derived MOM. Fluorescent staining of surfactant-C (FIG. 2D) in 21 day cultures reveals characteristic localized expression of the alveolar specific protein within the alveolar structures formed in the matrix.

Tissue-specific gene expression: PCR analysis of gene expression in cells cultured on liver- or lung-derived micro-organ matrices revealed strong interaction between the matrix and the cultured cells. Expression of all of the liver specific genes tested (albumin, FactorV, α-GST, GS and MUP) was detected in primary hepatocytes cultured for 21 days on liver-derived MOMs (FIG. 3A, LiMOM+H), while expression of only FactorV, but no expression of α-GST, GS and MUP was detected in hepatocytes cultured on lung-derived MOMs (FIG. 3A, LMOM+H). Expression of all of the lung specific genes tested (surfactant-protein C, surfactant-protein D, aquaporin-5 and T1-α) was detected in AII-P lung progenitors cultured for 21 days on lung-derived MOMs (FIG. 3B, LMOM+AP), while no expression of surfactant-C, surfactant-D or aquaporin-5 was detected in AII-P lung progenitors cultured on liver-derived MOMs (FIG. 3B, LiMOM+AP).

Example II

Functional, Glucose-Responsive Islets from Islets of Langerhans Grown on Pancreas-Derived MOMs Pancreatic islets are organized in a characteristic acinar structure, and do not typically retain islet architecture, or glucose-responsive insulin secretion when grown in long-term primary culture. The ability of devitalized, acellular micro-organ matrices (MOMs) to support growth and tissue-specific function of islets was tested by seeding isolated islets on pancreas-derived MOMs.

Islet beta cells, in contrast to the exocrine pancreatic cells, do not form a basement membrane. Instead, pancreatic islets are surrounded by a continuous peri-insular basement membrane deposited by endothelial cells that contains collagen IV and laminin, thought to promote insulin gene expression and proliferation in beta cells. Acellular, devitalized micro-organ matrices prepared from fresh pancreata of adult, C57/b mice as described herein retain the architecture characteristic of normal pancreas tissue (FIGS. 4A and 4B). Staining of the whole mounts of the pancreas MOMs for laminin (green fluorescence) revealed a laminin-rich acinar basement membrane pattern typically found surrounding an acinus and islet (FIG. 4B, arrows). Upon higher magnification, the typical architecture derived from islet vasculature is evident in the membrane structure of the acellular pancreatic MOM (FIG. 4C, arrows).

In order to determine whether pancreatic MOMs could sustain pancreatic islet cells in culture, isolated pancreatic islets were seeded onto the pancreas-derived MOMs and maintained in culture for up to 78 days.

Microscopic observation revealed that the seeded islet cells first attach to the pancreatic MOMs, gradually growing to cover the inner and outer surfaces of the MOMs. At 10 days culture, extensive outgrowths of islet-specific Pdx1+ cells originating from the original seeded islets are evident throughout the islet-pancreatic-MOMs (FIGS. 5B, 5C and 5D). When 10 day cultured islet-MOMs were fixed and stained, a high percentage of proliferating islet cells within islet-pancreas-MOM culture was observed throughout using the cell-cycling marker Ki67 (FIG. 5E). Higher magnification of outgrowths in the fixed preparations revealed widespread Pdx1 expression within the outgrowths (FIGS. 5F, 5G).

Transverse sections through the 10 day cultured islet-MOMs revealed functional integrity of the islets when cultured on pancreatic MOMs. DAPI (nuclear) staining showed islet cells proliferating throughout the depths of the pancreatic MOMs (FIG. 6A, blue), while insulin-specific staining (FIG. 6A, red) revealed numerous, diffusely organized insulin-secreting cells within the growing islet cells. When the same islet-pancreatic MOM cultures were observed after 78 days in culture, the presence of dense cell growth throughout the islet-MOM (FIG. 6B, blue) comprising numerous clusters of insulin-secreting cells (FIG. 6B, red) indicated that pancreas-derived MOMs can support viable, actively growing and functionally competent islet culture in both short- and long-term culture.

In order to determine whether islet cells seeded individually on pancreas MOMs would proliferate and maintain function in culture, pancreatic islets from transgenic mice expressing GFP under transcriptional control of the islet-specific Pdx1 promoter were dissociated before seeding on pancreatic MOMs (approx. $5-8 \times 10^3$ islet cells per MOM). Viable, green fluorescing cells were observed throughout the MOMs at 1 day after seeding (FIG. 7A), and in clearly organized clusters by day 13 of culture (FIG. 7B), which became denser and more distinct by day 17 of culture (FIG. 7C). Quantitation of the portion of cells actively expressing the Pdx1-GFP transgene indicated that roughly between 20% and 50% of the islet cells populating the pancreatic MOMs retained tissue-specific gene expression (FIGS. 7D, 7E and 7F).

Thus, pancreatic micro-organ matrices can support long term growth and proliferation of functional pancreatic islets and pancreatic islet cells in culture.

Long-term glucose-responsive pancreatic islet cell culture on pancreatic MOMs: The hallmark of functional pancreatic islets is the ability sense glucose levels and regulate insulin secretion accordingly. Typically, this function is lost during culture.

In order to determine the extent of retention of natural islet function, the response of islets cultured on pancreatic MOMs to increased glucose concentration was assessed. When 50 day cultured islet-pancreas MOMs were transferred from hypoglycemic (3 mM glucose) to hyperglycemic (16.7 mM glucose) conditions, a greater than two-fold increase in insulin secretion (measured by ELISA) was detected (FIG. 8), indicating maintenance of normal insulin production and glucose responsive secretion in long term islet-pancreatic MOM culture.

Example III

Long Term Islet-Specific Spatial and Functional Organization of Pancreatic Islet Cells on Non-Homologous MOMs Culture of pancreatic islets and islet cells, and maintenance of physiological function is a critical goal for restorative therapy in diabetes. In order to determine whether islet cells can proliferate and maintain function when cultured on micro-organ matrices derived from other than pancreatic sources, isolated, dissociated islet cells were seeded on lung-derived MOMs and cultured as described in Example H. The characteristic spatial distribution of islet cell function and insulin and glucose transporter 2 (Glut2) protein expression was detected in intermediate and long term islet-lung MOM cultures.

When long term islet cell-lung MOM cultures were examined for expression of insulin (red fluorescence, FIGS. 9B, 9D, 9E, 10B, 10D, 10F and 10H) and Glut2 (green fluorescence, FIGS. 9C, 9D, 9E, 10D, 10C, 10G and 10H), islet specific gene expression was detected among clusters of cells. At 14 days culture (FIGS. 10A-10D), indication of clustering of insulin and Glut2 expressing cells is evident. By 50 days culture (FIGS. 10E-10H), cell proliferation is evident, and stronger expression of insulin and Glut2 in the clusters is detected. At 60 days culture, cell density on the lung MOM is greater, and expression of insulin and Glut2 more widespread, but still concentrated in clusters (FIGS. 9A-9E). When viewed together, the distribution of insulin and Glut2 expressing cells overlap nearly completely, at all culture durations studied (FIGS. 9D, 9E, 10D and 10H).

Thus, culture of islets on non-homologous, lung MOMs provides organ-specific spatial distribution of the seeded cells, robust proliferation and coordinated expression of critical, islet-specific functions throughout short, intermediate and long-term culture conditions.

Example IV

Vascularization of Transplanted Islet-Pancreatic MOMs

Vascularization is critical to survival and function of transplanted islets. When islet-pancreatic MOMs cultured for 20 days ex-vivo were implanted subcutaneously into syngeneic mouse hosts, induction of vascularization was obvious, already 15 days following transplantation (FIG. 11), indicating the strong in-vivo angiogenic effect of pancreatic MOMs and MOM culture on the transplanted islets.

Example V

Islet-Specific Gene Expression in Embryonic Stem Cells Grown on MOMs

In order to determine the ability of devitalized, acellular micro-organ matrices (MOMS) to support growth of totipotent embryonic stem cells, and the effect of culture on MOMs on their tissue specific differentiation, human embryonic stem cells (hES) were seeded on MOMs, and proliferation and tissue-specific function of the cultured hES were tested.

Cultured human embryonic stem cells were seeded on pancreatic MOMs and observed after 17 and 20 days in hES-pancreatic-MOM culture. Immunodetection of cell proliferation (DAPI, blue fluorescence, FIGS. 12A, 12B and 13A) and insulin (red fluorescence, FIGS. 12A, 12B and 13A) revealed that after 17 days in culture on the pancreatic MOMs, hES cells proliferated vigorously (FIGS. 12A, 13A), with clusters of differentiated cells clearly expressing insulin (red fluorescence, FIGS. 12A, 13A). After 20 days in culture with the pancreatic MOMs, proliferation and clusters of insulin expression hES cells were also observed within the depths of the pancreatic MOM (FIG. 12B).

In order to test the effect of micro-organ matrices of various origins on hES culture and development in-vitro, hES cells were seeded on micro-organ matrices prepared as described herein from liver, pancreas and lung tissue, and cultured for up to 21 days. Assay of expression of the tissue-specific markers albumin (liver), insulin (pancreatic islets) and prosurfactant-B (lung alveolar cells) revealed that culture of the hES on micro-organ matrices of diverse origin resulted in partial selective differentiation of the hES cells, with the lung and pancreas-derived MOMs being most restrictive.

Peptide composition of MOMs of diverse origin: In order to further characterize MOMs of different tissue origin, the peptide composition of the decellarularized MOMs was assessed. Component peptides were generated by denaturation of the MOMs in 8M urea and digestion by trypsin. Sequence determination of resulting peptides was carried out by liquid chromatography-mass spectrometry (LC-MS/MS) using an Orbitrap Mass Spectrometer (Thermo Scientific) and the sequenced peptides were identified by Pep-Miner (IBM, Israel) and Sequest (Thermo Finnegan) software.

Comparing the peptide composition of pancreas-derived MOMs with MOMs derived from liver, lung and pancreas revealed that MOMs from different tissue origins are characterized by individual peptide profiles (Table 2). For example laminin alpha-5 was found in lung-derived MOMs and in liver-derived MOMs but not in pancreas-derived MOMs, while laminin alpha-2 was detected in pancreas-derived MOMs and liver-derived MOMs but not in lung-derived MOMs.

Example VI

Micro-Organ Matrices MOM from Cryopreserved Tissue

In order to determine the ability of frozen, rather than fresh tissue to provide devitalized, acellular micro-organ matrices (MOMs) for culture and transplantation, pancreatic micro-organ matrices were prepared from cryopreserved pig pancreas columns, as described herein.

FIG. 14A shows a 300 μM-thick MO prepared from washed, cyropreserved pig pancreas tissue 7-9 mm long, 5-8 wide, 300 micron thick, before decellularization treatment. FIG. 14B shows the MO following decellularization in detergent.

Example VII

Large-Scale Micro-Organ Matrices MOM

In order to determine the ability of large sections of devitalized, acellular tissue-derived micro-organ scaffolds to support cell proliferation, vitality and cell-specific structural integrity and function, large (12×12 mm) pancreatic micro-organ matrices were prepared from fresh pig pancreas columns, as described herein.

When the pig pancreatic MOMs were seeded with fluorescent human MDA-MB-231/GFP breast carcinoma cells at a density of 2×10⁵ cells/well/MOM, attachment to the MOMs was observed as soon as day 1 of culture (FIGS. 15A and 15B). After 7 days in culture, proliferation and penetration of the cells to the depths of the pancreatic MOMs was

TABLE 2

| | |
|---|---|
| filamin, alpha [Mus musculus] | LIVER |
| integrin alpha 3 [Mus musculus] | LIVER |
| integrin alpha8 [Mus musculus] | LIVER |
| Integrin alpha-IIb precursor (Platelet membrane glycoprotein IIb) (GPalpha IIb) (GPIIb) (CD41 antige . . . | LIVER |
| integrin beta 1 (fibronectin receptor beta) [Mus musculus] | LIVER |
| intercellular adhesion molecule [Mus musculus] | LIVER |
| intermediate filament protein nestin [Mus musculus] | LIVER |
| latent transforming growth factor beta binding protein 4 [Mus musculus] | LIVER |
| LIM and calponin homology domains 1 [Mus musculus] | LIVER |
| mCG7631, isoform CRA_b [Mus musculus] | LIVER |
| moesin [Bos taurus] | LIVER |
| PREDICTED: laminin, alpha 3 isoform 1 [Mus musculus] | LIVER |
| PREDICTED: tensin 1 [Mus musculus] | LIVER |
| defender against cell death 1 [Homo sapiens] | PANCREAS |
| Elastase 1, pancreatic [Mus musculus] | PANCREAS |
| elastase 2 [Mus musculus] | PANCREAS |
| elastase 3, pancreatic [Mus musculus] | PANCREAS |
| agrin [Mus musculus] | LIVER, LUNG |
| alpha-1(XVIII) collagen [Mus musculus] | LIVER, LUNG |
| ankycorbin [Mus musculus] | LIVER, LUNG |
| biglycan [Mus musculus] | LIVER, LUNG |
| collagen type XIV [Mus musculus] | LIVER, LUNG |
| dermatopontin [Mus musculus] | LIVER, LUNG |
| laminin, alpha 5 [Mus musculus] | LIVER, LUNG |
| lectin, galactose binding, soluble 9 [Mus musculus] | LIVER, LUNG |
| lumican [Mus musculus] | LIVER, LUNG |
| laminin B1 subunit 1 [Mus musculus] | LIVER, PANCREAS |
| laminin, alpha 2 [Mus musculus] | LIVER, PANCREAS |
| Clusterin precursor (Sulfated glycoprotein 2) (SGP-2) (Clustrin) (Apolipoprotein J) (Apo-J) [Contain . . . | LIVER, LUNG, PANCREAS |
| collagen, type I, alpha 1 [Mus musculus] | LIVER, LUNG, PANCREAS |
| decorin [Mus musculus] | LIVER, LUNG, PANCREAS |
| fibronectin 1 [Mus musculus] | LIVER, LUNG, PANCREAS |
| gelsolin [Mus musculus] | LIVER, LUNG, PANCREAS |
| Laminin subunit beta-2 precursor (S-laminin) (S-LAM) | LIVER, LUNG, PANCREAS |
| laminin, alpha 4 [Mus musculus] | LIVER, LUNG, PANCREAS |
| laminin, gamma 1, isoform CRA_b [Mus musculus] | LIVER, LUNG, PANCREAS |
| PREDICTED: perlecan (heparan sulfate proteoglycan 2) [Mus musculus] | LIVER, LUNG, PANCREAS |
| pro-alpha-2(I) collagen [Mus musculus] | LIVER, LUNG, PANCREAS |
| vimentin [Mus musculus] | LIVER, LUNG, PANCREAS | observed (FIGS. 15C and 15D). By day 15 of culture, the breast carcinoma cells could be seen proliferating and populating all surfaces of the pancreatic MOMs, clearly indicating the ability of large-scale pancreatic MOMs prepared to support growth and proliferation of cells in MOM culture.

Such large scale MOMs can be used to produce large syncytia of tissue-derived scaffolds, (e.g. 12×12 mm by 300 micometers), suited for therapeutic use. Such scaling up makes it possible to overcome morphological limitations imposed by the structure of sime tissues or organs.

Further, culture of the carcinoma cells on the large scale pancreatic MOMs illustrates that the MOMs, and even large scale MOMs of the invention, derived from normal tissue, can be used to culture cancerous as well as normal calls.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

---

What is claimed is:

1. A composition of matter comprising: (i) a devitalized, acellular, lung tissue-derived three dimensional scaffold having dimensions selected such that the point deepest within said scaffold is at least about 100 micrometers and not more than about 225 micrometers away from the nearest surface of the scaffold; and (ii) beta cells selected from beta cells isolated from pancreatic islets and beta cells differentiated in-vitro from stem and/or progenitor cells,
   wherein the beta cells are seeded and cultured on said acellular three dimensional scaffold and maintain glucose-responsive insulin secretion for at least 7 days of culture on said scaffold.

2. The composition of matter of claim 1, wherein said seeded beta cells are cultured beta cells.

3. The composition of matter of claim 1, wherein said seeded beta cells are cultured and expanded beta cells.

4. The composition of matter of claim 1, wherein said beta cells are beta cells differentiated from stem and/or progenitor cells.

5. The composition of matter of claim 1, wherein said beta cells express at least one beta cell-specific protein selected from the group consisting of insulin, Glut2 and Pdx1.

6. The composition of matter of claim 5, wherein said beta cells express Glut2 or Pdx1.

7. A method of generating the composition of matter of claim 1, the method comprising seeding said beta cells on said scaffold.

8. A pharmaceutical composition comprising the composition of matter of claim 1 and a pharmaceutically acceptable carrier.

9. A method of treating diabetes in a subject, comprising transplanting a therapeutically effective amount of the composition of matter of claim 1 into the subject, thereby treating diabetes.

10. A method of producing a beta cell-specific protein comprising in-vitro culturing the composition of matter of claim 1 under conditions which promote cell growth and proliferation, and isolating said beta cell-specific protein from said culture.

11. The composition of matter of claim 1, wherein said beta cells are characterized by glucose-responsive insulin secretion after at least 14 days of culture on the composition.

12. The composition of matter of claim 1, wherein said beta cells are characterized by glucose-responsive insulin secretion after at least 28 days of culture on the composition.

* * * * *